(12) United States Patent
Vaglio et al.

(10) Patent No.: US 11,164,673 B2
(45) Date of Patent: Nov. 2, 2021

(54) ATTACHING PATIENT CONTEXT TO A CALL HISTORY ASSOCIATED WITH VOICE COMMUNICATION

(71) Applicant: CERNER INNOVATION, INC., Kansas City, KS (US)

(72) Inventors: Jay Christopher Vaglio, Kansas City, KS (US); Matt Ryan Anderson, Kansas City, MO (US)

(*) Notice: Subject to any disclaimer, the term of this patent is extended or adjusted under 35 U.S.C. 154(b) by 380 days.

(21) Appl. No.: 14/551,555

(22) Filed: Nov. 24, 2014

(65) Prior Publication Data

US 2015/0081339 A1    Mar. 19, 2015

Related U.S. Application Data

(63) Continuation of application No. 13/711,217, filed on Dec. 11, 2012, now Pat. No. 8,948,734.

(Continued)

(51) Int. Cl.
| | |
|---|---|
| *G16H 40/67* | (2018.01) |
| *G08B 5/22* | (2006.01) |
| *G06F 3/048* | (2013.01) |
| *G06Q 50/00* | (2012.01) |
| *H04M 1/724* | (2021.01) |

(Continued)

(52) U.S. Cl.
CPC .............. *G16H 40/67* (2018.01); *G06F 3/048* (2013.01); *G06F 3/0482* (2013.01); *G06F 3/04817* (2013.01); *G06F 3/04842* (2013.01); *G06Q 50/00* (2013.01); *G08B 5/22* (2013.01); *H04M 1/724* (2021.01); *H04M 3/00* (2013.01); *H04W 4/16* (2013.01); *H04W 4/14* (2013.01); *H04W 4/90* (2018.02)

(58) Field of Classification Search
CPC ..................................................... G06F 3/0482
See application file for complete search history.

(56) References Cited

U.S. PATENT DOCUMENTS

| | | |
|---|---|---|
| 1,039,713 A | 10/1912 | Eaton |
| 4,237,344 A | 12/1980 | Moore |
| | (Continued) | |

FOREIGN PATENT DOCUMENTS

WO    2015/023674 A1    2/2015

OTHER PUBLICATIONS

Final Office Action dated Feb. 20, 2015 in U.S. Appl. No. 13/711,177, 11 pages.

(Continued)

*Primary Examiner* — Robert A Sorey
*Assistant Examiner* — Kristine K Rapillo
(74) *Attorney, Agent, or Firm* — Shook, Hardy & Bacon LLP

(57) ABSTRACT

Systems, methods, and computer-readable media for declining, attaching, and editing patient context to mobile voice communication are provided. Patient demographic or alert information is attached to items within call histories associated with voice communication which are stored in the EMR and utilized for later analysis (e.g., analytics, patient progress, billing, reimbursement, staff scheduling, patient acuity, and the like). In embodiments, the context is declined, attached, or edited to items from the call history. In embodiments, the context is attached to items in the call history when the voice communication is initiated.

18 Claims, 21 Drawing Sheets

Related U.S. Application Data

(60) Provisional application No. 61/710,409, filed on Oct. 5, 2012.

(51) Int. Cl.

| | | |
|---|---|---|
| *H04W 4/16* | (2009.01) | |
| *H04M 3/00* | (2006.01) | |
| *G06F 3/0482* | (2013.01) | |
| *G06F 3/0484* | (2013.01) | |
| *G06F 3/0481* | (2013.01) | |
| *H04W 4/90* | (2018.01) | |
| *H04W 4/14* | (2009.01) | |

(56) References Cited

U.S. PATENT DOCUMENTS

| | | | |
|---|---|---|---|
| 5,319,355 A | 6/1994 | Russek | |
| 5,319,363 A | 6/1994 | Welch et al. | |
| 5,534,851 A | 7/1996 | Russek | |
| 5,942,986 A | 8/1999 | Shabot et al. | |
| 5,999,846 A | 12/1999 | Pardey et al. | |
| 6,754,516 B2 | 6/2004 | Mannheimer | |
| 6,804,656 B1 | 10/2004 | Rosenfeld et al. | |
| 6,928,370 B2 | 8/2005 | Anuzis et al. | |
| 7,035,622 B2 | 4/2006 | Pappalardo et al. | |
| 7,035,623 B2 | 4/2006 | Pappalardo et al. | |
| 7,090,053 B2 | 8/2006 | Bothwell et al. | |
| 7,123,950 B2 | 10/2006 | Mannheimer | |
| 7,215,945 B2 | 5/2007 | Pappalardo et al. | |
| 7,224,281 B2 | 5/2007 | Santoso et al. | |
| 7,225,408 B2 | 5/2007 | O'Rourke | |
| 7,249,036 B2 | 7/2007 | Bayne | |
| 7,256,708 B2 | 8/2007 | Rosenfeld et al. | |
| D551,239 S | 9/2007 | Cummins et al. | |
| 7,307,543 B2 | 12/2007 | Rosenfeld et al. | |
| 7,315,825 B2 | 1/2008 | Rosenfeld et al. | |
| 7,321,862 B2 | 1/2008 | Rosenfeld et al. | |
| D577,734 S | 9/2008 | Ryu et al. | |
| 7,430,692 B2 | 9/2008 | White, III et al. | |
| 7,454,359 B2 | 11/2008 | Rosenfeld et al. | |
| 7,475,019 B2 | 1/2009 | Rosenfeld et al. | |
| D596,192 S | 7/2009 | Shotel | |
| D599,812 S | 9/2009 | Hirsch | |
| D599,813 S | 9/2009 | Hirsch | |
| D604,740 S | 11/2009 | Matheny et al. | |
| D607,004 S | 12/2009 | Kordus et al. | |
| D610,159 S | 2/2010 | Matheny et al. | |
| D625,317 S | 10/2010 | Jewitt et al. | |
| D631,891 S | 2/2011 | Vance et al. | |
| D636,402 S | 4/2011 | Vance et al. | |
| D640,276 S | 6/2011 | Woo | |
| 7,981,032 B2 | 7/2011 | Santoso et al. | |
| 8,015,030 B2 | 9/2011 | Brown | |
| 8,092,380 B2 | 1/2012 | Rothman et al. | |
| 8,100,829 B2 | 1/2012 | Rothman et al. | |
| 8,122,006 B2 | 2/2012 | de Castro Alves et al. | |
| D657,378 S | 4/2012 | Vance et al. | |
| 8,160,895 B2 | 4/2012 | Schmitt et al. | |
| 8,165,893 B1 | 4/2012 | Goldberg et al. | |
| 8,170,887 B2 | 5/2012 | Rosenfeld et al. | |
| 8,175,895 B2 | 5/2012 | Rosenfeld et al. | |
| D662,507 S | 6/2012 | Mori et al. | |
| D665,399 S | 8/2012 | Carpenter et al. | |
| 8,332,017 B2 | 12/2012 | Tarassenko et al. | |
| 8,355,925 B2 | 1/2013 | Rothman et al. | |
| 8,374,988 B2 | 2/2013 | Gawlick | |
| 8,401,606 B2 | 3/2013 | Mannheimer | |
| 8,401,607 B2 | 3/2013 | Mannheimer | |
| 8,403,847 B2 | 3/2013 | Rothman et al. | |
| 8,416,085 B2 | 4/2013 | Gawlick | |
| 8,417,233 B2* | 4/2013 | Woloshyn ............ G06F 3/0488 455/412.1 | |
| 8,417,662 B2 | 4/2013 | Gawlick | |
| D682,294 S | 5/2013 | Kanalakis, Jr. et al. | |
| D682,844 S | 5/2013 | Friedlander et al. | |
| D682,858 S | 5/2013 | Frijlink | |
| 8,451,101 B2 | 5/2013 | Somasundaram et al. | |
| 8,454,506 B2 | 6/2013 | Rothman et al. | |
| D686,221 S | 7/2013 | Brinda et al. | |
| D687,844 S | 8/2013 | Chaudhri | |
| 8,543,534 B2 | 9/2013 | Alves et al. | |
| D695,773 S | 12/2013 | Tagliabue et al. | |
| D696,682 S | 12/2013 | Kim et al. | |
| 8,615,291 B2 | 12/2013 | Moorman et al. | |
| 8,618,930 B2* | 12/2013 | Papadopoulos .... A61B 5/02427 340/539.12 | |
| D700,914 S | 3/2014 | Jin et al. | |
| D701,221 S | 3/2014 | Ahmed et al. | |
| D705,239 S | 5/2014 | Thompson et al. | |
| 8,775,196 B2* | 7/2014 | Simpson ............ G06F 19/3418 705/2 | |
| 8,838,196 B2 | 9/2014 | Mannheimer | |
| 8,842,001 B2 | 9/2014 | Gilham et al. | |
| D714,817 S | 10/2014 | Lee | |
| D715,820 S | 10/2014 | Rebstck | |
| 8,856,156 B1 | 10/2014 | McNair et al. | |
| D717,808 S | 11/2014 | Tsuru et al. | |
| 8,886,663 B2 | 11/2014 | Gainsboro et al. | |
| 8,886,792 B2 | 11/2014 | Biondi et al. | |
| D719,577 S | 12/2014 | Tsuru et al. | |
| D720,766 S | 1/2015 | Mandal et al. | |
| 8,948,734 B2 | 2/2015 | Vaglio et al. | |
| D726,202 S | 4/2015 | Zürn | |
| D731,528 S | 6/2015 | Nagasawa et al. | |
| D732,052 S | 6/2015 | Kim et al. | |
| D733,175 S | 6/2015 | Bae | |
| 9,052,809 B2 | 6/2015 | Vesto | |
| D734,349 S | 7/2015 | Amin et al. | |
| D734,350 S | 7/2015 | Inose et al. | |
| D736,789 S | 8/2015 | Tursi et al. | |
| 9,159,313 B2 | 10/2015 | Saeki et al. | |
| D742,909 S | 11/2015 | Lee et al. | |
| D743,414 S | 11/2015 | Shunock | |
| D743,416 S | 11/2015 | Lim et al. | |
| 9,185,202 B2 | 11/2015 | Herbst et al. | |
| D747,343 S | 1/2016 | Brinda et al. | |
| D751,097 S | 3/2016 | Sarafa et al. | |
| D752,604 S | 3/2016 | Zhang | |
| D752,614 S | 3/2016 | Kwon et al. | |
| 9,280,637 B2 | 3/2016 | Vaglio et al. | |
| D753,165 S | 4/2016 | Watson | |
| D753,707 S | 4/2016 | Yang | |
| D754,176 S | 4/2016 | Kim | |
| D754,679 S | 4/2016 | Gobinski et al. | |
| D757,771 S | 5/2016 | Drozd et al. | |
| D757,778 S | 5/2016 | Lemay | |
| D758,386 S | 6/2016 | Zhang | |
| D758,400 S | 6/2016 | Chang et al. | |
| D759,687 S | 6/2016 | Chang et al. | |
| D760,738 S | 7/2016 | Scalisi et al. | |
| 9,400,874 B2 | 7/2016 | Powell et al. | |
| D762,676 S | 8/2016 | Lim | |
| D763,290 S | 8/2016 | Gupta et al. | |
| D763,863 S | 8/2016 | Vymenets et al. | |
| D763,864 S | 8/2016 | Lu et al. | |
| D763,881 S | 8/2016 | Smith et al. | |
| D763,882 S | 8/2016 | Liang | |
| D764,511 S | 8/2016 | Han et al. | |
| D765,110 S | 8/2016 | Liang | |
| D766,294 S | 9/2016 | Smith | |
| D767,605 S | 9/2016 | Mensinger et al. | |
| 9,449,355 B2 | 9/2016 | Kozicki et al. | |
| D768,647 S | 10/2016 | Bauer et al. | |
| D770,491 S | 11/2016 | Jung | |
| D771,667 S | 11/2016 | Woo | |
| D771,670 S | 11/2016 | Chan et al. | |
| D772,259 S | 11/2016 | Pahwa et al. | |
| D772,921 S | 11/2016 | Jewitt et al. | |
| D774,521 S | 12/2016 | Amin | |
| D775,167 S | 12/2016 | Vazquez | |
| D777,184 S | 1/2017 | Yang et al. | |
| D777,758 S | 1/2017 | Kisselev et al. | |
| D778,929 S | 2/2017 | Mensinger et al. | |
| D779,517 S | 2/2017 | Pierson et al. | |

(56) References Cited

U.S. PATENT DOCUMENTS

| | | |
|---|---|---|
| D780,191 S | 2/2017 | Kelley |
| 9,582,978 B2 | 2/2017 | Herbst et al. |
| D781,315 S | 3/2017 | Wang |
| D784,384 S | 4/2017 | Hong et al. |
| D785,003 S | 4/2017 | Yun et al. |
| D785,008 S | 4/2017 | Lim et al. |
| D785,009 S | 4/2017 | Lim et al. |
| D785,012 S | 4/2017 | Jou |
| D785,029 S | 4/2017 | Gedrich et al. |
| 9,626,479 B2 | 4/2017 | Zaleski |
| 9,659,482 B2 | 5/2017 | Yang et al. |
| D789,947 S | 6/2017 | Sun |
| D789,949 S | 6/2017 | Sun |
| D789,956 S | 6/2017 | Ortega et al. |
| 9,706,966 B2 | 7/2017 | Colman et al. |
| 9,747,778 B2 | 8/2017 | Mukherji et al. |
| D797,753 S | 9/2017 | Agarwal |
| 9,805,573 B2 | 10/2017 | Herbst et al. |
| D804,493 S | 12/2017 | Daniel et al. |
| 9,836,940 B2 | 12/2017 | Herbst et al. |
| D807,899 S | 1/2018 | Hilhorst et al. |
| 9,881,475 B2 | 1/2018 | Herbst et al. |
| D810,115 S | 2/2018 | Chaudhri et al. |
| D812,067 S | 3/2018 | Chaudhri et al. |
| 9,911,300 B2 | 3/2018 | Herbst et al. |
| 9,924,908 B2 | 3/2018 | Hubert et al. |
| D819,067 S | 5/2018 | Behzadi et al. |
| 10,037,411 B2 | 7/2018 | Bala et al. |
| D834,043 S | 11/2018 | Di Nicola et al. |
| 10,121,346 B2 | 11/2018 | Herbst et al. |
| D835,664 S | 12/2018 | Chaudhri et al. |
| 10,176,690 B2 | 1/2019 | Herbst et al. |
| D841,660 S | 2/2019 | Mercado |
| D844,635 S | 4/2019 | Spångberg |
| 10,275,570 B2 | 4/2019 | Norton et al. |
| 10,379,713 B2 | 8/2019 | Vaglio et al. |
| 10,388,413 B2 | 8/2019 | Bala et al. |
| D859,442 S | 9/2019 | Zhang et al. |
| D879,111 S | 3/2020 | Zeng et al. |
| 10,580,279 B2 | 3/2020 | Herbst et al. |
| 10,607,728 B2 | 3/2020 | Agassi et al. |
| D882,583 S | 4/2020 | Dattilo-Green et al. |
| 10,642,460 B2 | 5/2020 | Vaglio et al. |
| D887,439 S | 6/2020 | Elgena |
| 10,699,812 B2 | 6/2020 | Bala et al. |
| D890,795 S | 7/2020 | Kouno et al. |
| 2002/0040282 A1 | 4/2002 | Bailey et al. |
| 2002/0062230 A1 | 5/2002 | Morag et al. |
| 2003/0163789 A1 | 8/2003 | Blomquist |
| 2003/0191730 A1 | 10/2003 | Adkins et al. |
| 2004/0073453 A1 | 4/2004 | Nenov et al. |
| 2004/0172222 A1 | 9/2004 | Simpson et al. |
| 2005/0065817 A1 | 3/2005 | Mihai et al. |
| 2005/0146431 A1 | 7/2005 | Hastings et al. |
| 2005/0151640 A1 | 7/2005 | Hastings |
| 2006/0049936 A1 | 3/2006 | Collins et al. |
| 2006/0161457 A1 | 7/2006 | Rapaport et al. |
| 2007/0239488 A1 | 10/2007 | DeRosso |
| 2008/0021709 A1 | 1/2008 | Greer |
| 2008/0027288 A1* | 1/2008 | Renz ............... A61B 5/0002 600/300 |
| 2008/0074951 A1 | 3/2008 | Hubicki |
| 2009/0048868 A1 | 2/2009 | Portnoy et al. |
| 2009/0197635 A1 | 8/2009 | Kim et al. |
| 2010/0001838 A1 | 1/2010 | Miodownik et al. |
| 2010/0123587 A1 | 5/2010 | Walls |
| 2010/0137693 A1 | 6/2010 | Porras et al. |
| 2010/0223071 A1 | 9/2010 | Kland et al. |
| 2011/0001605 A1 | 1/2011 | Kiani et al. |
| 2011/0054946 A1 | 3/2011 | Coulter et al. |
| 2011/0105979 A1 | 5/2011 | Schlaeper et al. |
| 2011/0106560 A1 | 5/2011 | Eaton, Jr. et al. |
| 2011/0196306 A1 | 8/2011 | De La Huerga |
| 2011/0208816 A1 | 8/2011 | Chavez |
| 2011/0276396 A1 | 11/2011 | Rathod |
| 2011/0295621 A1 | 12/2011 | Farooq et al. |
| 2012/0075103 A1 | 3/2012 | Powell et al. |
| 2012/0101847 A1 | 4/2012 | Johnson et al. |
| 2012/0169467 A1 | 7/2012 | Condra |
| 2012/0185547 A1 | 7/2012 | Rugg et al. |
| 2012/0278104 A1 | 11/2012 | Traughber et al. |
| 2012/0284040 A1 | 11/2012 | Dupin |
| 2013/0009783 A1 | 1/2013 | Tran |
| 2013/0049950 A1 | 2/2013 | Wohlert |
| 2013/0065569 A1 | 3/2013 | Leipzig et al. |
| 2013/0085765 A1 | 4/2013 | Tuchinda et al. |
| 2013/0085798 A1* | 4/2013 | Spatola ............... G16H 40/20 705/7.24 |
| 2013/0096953 A1 | 4/2013 | Beverly et al. |
| 2013/0103768 A1 | 4/2013 | Freebeck |
| 2013/0104077 A1 | 4/2013 | Felt |
| 2013/0162424 A1 | 6/2013 | Treacy |
| 2013/0183923 A1 | 7/2013 | Brackett et al. |
| 2013/0297348 A1 | 11/2013 | Cardoza et al. |
| 2014/0039351 A1 | 2/2014 | Mix et al. |
| 2014/0051399 A1* | 2/2014 | Walker ............... H04L 65/1059 455/412.1 |
| 2014/0070939 A1 | 3/2014 | Halverson et al. |
| 2014/0085080 A1 | 3/2014 | Carnes |
| 2014/0097961 A1 | 4/2014 | Vaglio et al. |
| 2014/0099929 A1 | 4/2014 | Vaglio et al. |
| 2014/0100873 A1 | 4/2014 | Vaglio et al. |
| 2014/0132413 A1 | 5/2014 | Fox et al. |
| 2014/0172996 A1 | 6/2014 | Deeter et al. |
| 2014/0184408 A1 | 7/2014 | Herbst et al. |
| 2014/0337442 A1 | 11/2014 | Zhuang et al. |
| 2014/0358585 A1 | 12/2014 | Reiner |
| 2015/0137968 A1 | 5/2015 | Rusin et al. |
| 2015/0148617 A1 | 5/2015 | Friedman |
| 2015/0254957 A1 | 9/2015 | Wilson et al. |
| 2016/0027277 A1 | 1/2016 | Herbst et al. |
| 2016/0110040 A1 | 4/2016 | Vaglio et al. |
| 2016/0360160 A1 | 12/2016 | Eizenberg |
| 2017/0024091 A1 | 1/2017 | Hosier, Jr. |
| 2017/0032093 A1 | 2/2017 | Norton et al. |
| 2017/0098037 A1 | 4/2017 | Agassi et al. |
| 2017/0109018 A1 | 4/2017 | Vaglio et al. |
| 2017/0109989 A1 | 4/2017 | Herbst et al. |
| 2017/0193801 A1 | 7/2017 | Bala et al. |
| 2017/0265819 A1 | 9/2017 | Colman et al. |
| 2017/0287300 A1 | 10/2017 | Herbst et al. |
| 2017/0352237 A1 | 12/2017 | Herbst et al. |
| 2017/0352238 A1 | 12/2017 | Herbst et al. |
| 2018/0102036 A1 | 4/2018 | Herbst et al. |
| 2018/0110477 A1 | 4/2018 | Collins et al. |
| 2018/0144598 A1 | 5/2018 | Herbst et al. |
| 2018/0153455 A1 | 6/2018 | Guazzi et al. |
| 2018/0315428 A1 | 11/2018 | Johnson et al. |
| 2018/0335903 A1 | 11/2018 | Coffman et al. |
| 2019/0066841 A1 | 2/2019 | Bala et al. |
| 2019/0244506 A1 | 8/2019 | Herbst et al. |
| 2020/0090806 A1 | 3/2020 | Bala et al. |
| 2020/0152038 A1 | 5/2020 | Herbst et al. |

OTHER PUBLICATIONS

Non-Final Office Action dated Mar. 17, 2015 in U.S. Appl. No. 13/711,206, 8 pages.
Non-Final Office Action dated Jul. 8, 2015 in U.S. Appl. No. 13/711,177, 5 pages.
Final Office Action dated Oct. 2, 2015 in U.S. Appl. No. 13/711,206, 15 pages.
Notice of Allowance dated Oct. 29, 2015 in U.S. Appl. No. 13/711,177, 9 pages.
Non-Final Office Action dated Feb. 25, 2016 in U.S. Appl. No. 13/711,206, 17 pages.
Final Office Action dated Nov. 3, 2016 in U.S. Appl. No. 13/711,206, 20 pages.
Final Office Action dated Jul. 7, 2014 in U.S. Appl. No. 13/711,177, 12 pages.
First Action Interview Pilot Program Pre-Interview Communication dated Sep. 25, 2014 in U.S. Appl. No. 13/711,206, 5 pages.

(56) References Cited

OTHER PUBLICATIONS

Notice of Allowance dated Sep. 29, 2014 in U.S. Appl. No. 13/711,217, 7 pages.
Non-Final Office Action dated Mar. 23, 2017 in U.S. Appl. No. 13/711,206, 10 pages.
How to Set Up Zoom on Android, http://blog.recovery-android.com/set-up-zoom-in-android/, Jan. 14, 2016, 3 pages.
ExDialer Dialer & Contacts, Modoohut Communication, Android Apps on Google Play Accessed Apr. 24, 2017 at: https://play.google.com/store/apps/details?id=com.modoohut.dialer&hl=en, 3 pages.
How to download Skype app on Android and do Voice and video chat, Oct. 29, 2012, 5 pages. Available at: http://www.howto-connect.com/how-to-download-skype-app-on-android-and-do-voice-and-video-chat/.
Contactive—A Caller ID App that Showcases Android's Openess, 3 pages. Accessed Apr. 24, 2017 at: http://techdomino.com/contactive-a-caller-id-app-that-showcases-androids-openess/.
Review: Our Favourite Effective Contact Managers, Contaker Blog, 6 pages. Accessed Apr. 24, 2017 at:http://blog.contaker.com/?p=61.
How to Design an iPhone App in Photoshop, by Tony Thomas, dated Oct. 26, 2011, medialoot.com [online], [retrieved Jul. 3, 2017], Available from internet UR: https://medialoot.com/blog/how-to-design-an-iphone-app-in-photoshop/.
Non-Final Office Action dated Jul. 13, 2017 in Design U.S. Appl. No. 29/602,910, 14 pages.
Notice of Allowance dated Jul. 19, 2017 in Design U.S. Appl. No. 29/602,800, 15 pages.
Final Office Action dated Jul. 27, 2017 in U.S. Appl. No. 13/711,206, 14 pages.
First Action Interview Office Action dated Aug. 9, 2017 in U.S. Appl. No. 14/551,555, 8 pages.
Find and replace pop-up window, by Jerome Detraz, dated Jul. 17, 2013, sketchappsource.com [online], [retrieved Jul. 3, 2017]. Available from internet <URL: https://web.archive.org/web/2130717090053/https://www.sketchappsources.com/free-source/190-find-replace-pop-up-window.html.
First Action Interview Preinterview Communication dated Dec. 4, 2014 in U.S. Appl. No. 13/731,191, 5 pages.
First Action Interview Office Action dated Jun. 3, 2015 in U.S. Appl. No. 13/731,191, 4 pages.
Non-Final Office Action dated Sep. 8, 2016 in U.S. Appl. No. 14/877,808, 7 pages.
Notice of Allowance dated Jan. 5, 2017 in U.S. Appl. No. 14/877,808, 5 pages.
First Action Interview Pre-Interview Communication dated Aug. 17, 2017 in U.S. Appl. No. 15/392,926, 5 pages.
Non-Final Office Action dated Sep. 21, 2017 in U.S. Appl. No. 15/630,617, 7 pages.
Notice of Allowance dated Sep. 28, 2017 in U.S. Appl. No. 15/392,926, 9 pages.
Notice of Allowance dated Oct. 30, 2017 in U.S. Appl. No. 15/630,617, 7 pages.
First Action Interview Pre-Interview Communication dated Nov. 15, 2017 in U.S. Appl. No. 15/684,565, 5 pages.
First Action Interview Pre-Interview Communication dated Nov. 30, 2017 in U.S. Appl. No. 15/684,563, 5 pages.
Notice of Allowance dated Dec. 19, 2017 in U.S. Appl. No. 15/684,565, 9 pages.
Notice of Allowance dated Jan. 10, 2018 in U.S. Appl. No. 15/684,563, 5 pages.
Final Office Action dated Mar. 2, 2018 in U.S. Appl. No. 29/602,910, 13 pages.
Clinical Workflow Solutions Extension HealthAlert brochure published by NEC Corporation Sep. 17, 2012.
Press Release by Extension Healthcare entitled: "Arc Solutions and Extension, Inc. Announce New Collaboration Software Solutions, Specifically Designed for the Healthcare Sector", Jan. 7, 2010.
Extension Mobile for Enterprise Healthcare Organizations Now Available on Apple iPhone and iPod Touch Via Apple AppStore, http://www.extensionhealthcare.com, Extension, Inc., Fort Wayne, IN, Jan. 10, 2011, 2 pages.
Extension, Inc. and AeroScout Partner to Deliver Solutions for Healthcare RTLS and VoIP, http://www.extensionhealthcare.com, Extension, Inc., Fort Wayne, IN, Feb. 19, 2010, 2 pages.
Extension, Inc. Launches New Interactive Communications Solution, http://www.extensionhealthcare.com, Extension, Inc., Fort Wayne, IN, May 25, 2011, 3 pages.
The American Hospital Association Endorses the Extension Healthid smart card system, http://www.news-medical.net, Published Aug. 21, 2009, 2 pages.
How to create a cool and usable CSS3 search box, dated Feb. 18, 2011, catalin.red [online], [retrieved Feb. 23, 2018]. Retrieved from internet <URL:https://catalin.red/how-to-create-a-cool-and-usable-css3-search-box/> (Year: 2011).
How to Add Search Bar in Table View, by Simon NG, dated Jul. 8, 2012, appcoda.com [online], [retrieved Feb. 23, 2018]. Retrieved from internet <URL:https://www.appcoda.com/how-to-add-search-bar-uitableview/> (Year: 2012).
First Action Interview Pre-Interview Communication dated Jun. 30, 2017 in U.S. Appl. No. 15/131,231, 5 pages.
Notice of Allowance dated Jan. 30, 2018 in U.S. Appl. No. 15/131,231, 7 pages.
Non-Final Office Action dated Apr. 24, 2018 in U.S. Appl. No. 14/875,800, 22 pages.
Notice of Allowance dated Apr. 25, 2018 in U.S. Appl. No. 15/131,231, 5 pages.
Riano et al., "MPM: A Knowledge-based functional model of medical practice", Journal of Biomedical Informatics 46 (2013) 379-387.
First Action Interview Pre-Interview Communication dated Jul. 6, 2018 in U.S. Appl. No. 14/983,685, 9 pages.
Non-Final Office Action dated Aug. 15, 2018 in U.S. Appl. No. 15/290,443, 7 pages.
Non-Final Office Action dated Jul. 25, 2018 in U.S. Appl. No. 15/837,856, 7 pages.
Non-Final Office Action dated Jul. 26, 2018 in U.S. Appl. No. 15/873,158, 6 pages.
Final Office Action dated Sep. 17, 2018 in U.S. Appl. No. 14/875,800, 20 pages.
Notice of Allowance dated Sep. 24, 2018 in U.S. Appl. No. 15/873,158, 5 pages.
Notice of Allowance dated Sep. 24, 2018 in U.S. Appl. No. 15/837,856, 5 pages.
Notice of Allowance received for U.S. Appl. No. 14/983,685, dated Mar. 12, 2019, 10 pages.
Non-Final Office Action received for U.S. Appl. No. 16/179,096, dated Sep. 3, 2019, 7 pages.
Final Office Action received for U.S. Appl. No. 15/395,603, dated Dec. 16, 2019, 9 pages.
Notice of Allowance received for U.S. Appl. No. 14/875,800, dated Nov. 25, 2019, 9 pages.
Non-Final Office Action received for U.S. Appl. No. 16/743,029, dated Apr. 1, 2020, 9 pages.
Non-Final Office Action received for U.S. Appl. No. 29/618,709, dated Aug. 6, 2020, 14 pages.
Non-Final Office Action received for U.S. Appl. No. 16/828,361, dated Sep. 4, 2020, 10 pages.

* cited by examiner

ATTACHING PATIENT CONTEXT TO A CALL HISTORY ASSOCIATED WITH VOICE COMMUNICATION

CROSS REFERENCE TO RELATED APPLICATIONS

This application is a continuation application of application Ser. No. 13/711,217, filed Dec. 11, 2012, which is entirely incorporated herein by reference. The Ser. No. 13/711,217 patent application claims the benefit of U.S. Provisional Application No. 61/710,409, titled "MULTI-ACTION BUTTON FOR MOBILE DEVICES AND ATTACHING PATIENT CONTEXT TO A CALL HISTORY," filed Oct. 5, 2012, which is hereby expressly incorporated by reference in its entirety. This application is related by subject matter to U.S. application Ser. No. 13/711,206 (Attorney Docket Number CRNI.175525), entitled "ATTACHING PATIENT CONTEXT TO A CALL HISTORY ASSOCIATED WITH VOICE COMMUNICATION", which is commonly assigned and filed on even date herewith, and is herein incorporated by reference in its entirety.

BACKGROUND

Patient medical information, such as that contained in the EMR, allows health care providers to provide continuity of care to patients. Thus, it is critical for clinicians providing care to patients to review and collaborate with other clinicians for each patient's medical record. However, these collaborations, while important to providing care for patients, often goes undocumented because the ability to track mobile voice communication as well as the content discussed is not currently available. This results in confusion and an inability to reference the details (e.g. patient name, relevant alerts, and the like) of a mobile voice call and leaves the clinician and healthcare entity unable to appropriately track such information that may otherwise be useful in analytics, tracking patient progress, billing, reimbursement, scheduling staff, and patient acuity.

Further, when receiving alerts regarding a particular patient, it is critical that these alerts are acknowledged in a timely manner. Often, it is necessary for an additional action to be taken in addition to acknowledging the alert. For example, the responding clinician may need to acknowledge (i.e., accept) the alert and call or text another clinician. Unfortunately, displays of current mobile devices are cluttered with option buttons which results in confusion and time lost pondering the correct action.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to declining, attaching, and editing patient context to mobile voice communication. More particularly, patient demographic or alert information is attached to a call history which is stored in the electronic medical record (EMR) and utilized for later analysis (e.g., analytics, patient progress, billing, reimbursement, staff scheduling, patient acuity, and the like).

Accordingly, in one embodiment, computer storage media storing computer-executable instructions that, when executed by one or more computing devices, cause the one or more computing devices to perform a method that facilitates declining, attaching, or editing patient context for a call history associated with mobile voice communication is provided. A selection of an item from a call history associated with voice communication is received. A selection to decline, attach, or edit context associated with the item is received. Upon receiving the selection to attach or edit context, a selection of the context comprising an alert, one or more patients, or a combination thereof to add or edit is received. The context associated with the item is attached or edited in accordance with the selection of the context.

In another embodiment, a computer system to facilitate declining, attaching, or editing patient context for a call history associated with mobile voice communication is provided. The computer system comprises a processor coupled to a computer storage medium, the computer storage medium having stored thereon a plurality of computer software components executable by the processor. An item selection component receives a selection of an item from a call history associated with voice communication. An edit component receives a selection to decline, attach, or edit context associated with the item. A context selection component that, upon receiving the selection to attach or edit context, receives a selection of the context comprising an alert, one or more patients, or a combination thereof. An attach component that attaches or edits the context associated with the item in accordance with the selection of the context.

In another embodiment, computer storage media having computer-executable instructions embodied thereon that, when executed, produce a graphical user interface (GUI) to facilitate declining, attaching, or editing patient context for a call history associated with mobile voice communication is provided. A call history display area displays a call history associated with voice communication. A selection display area displays an indicator for selecting to decline, attach, or edit context to an item associated with the call history. A context display area displays, upon selecting to attach or edit context, context comprising an alert, one or more patients, or a combination thereof to associate with the item. An attach component displays context associated with the item in accordance with the selection of the context.

BRIEF DESCRIPTION OF THE DRAWING

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention can positively impact health organizations' key imperatives in a variety of ways. Embodiments of the present invention provide context to voice communications that can be utilized in analytics, revealing trends, tracking resources, tracking patient progress, billing, reimbursement, scheduling staff, and patient acuity. Embodiments of the present invention provide multi-action buttons on mobile devices that can be utilized by clinicians to improve response time and availability.

Figure 1:
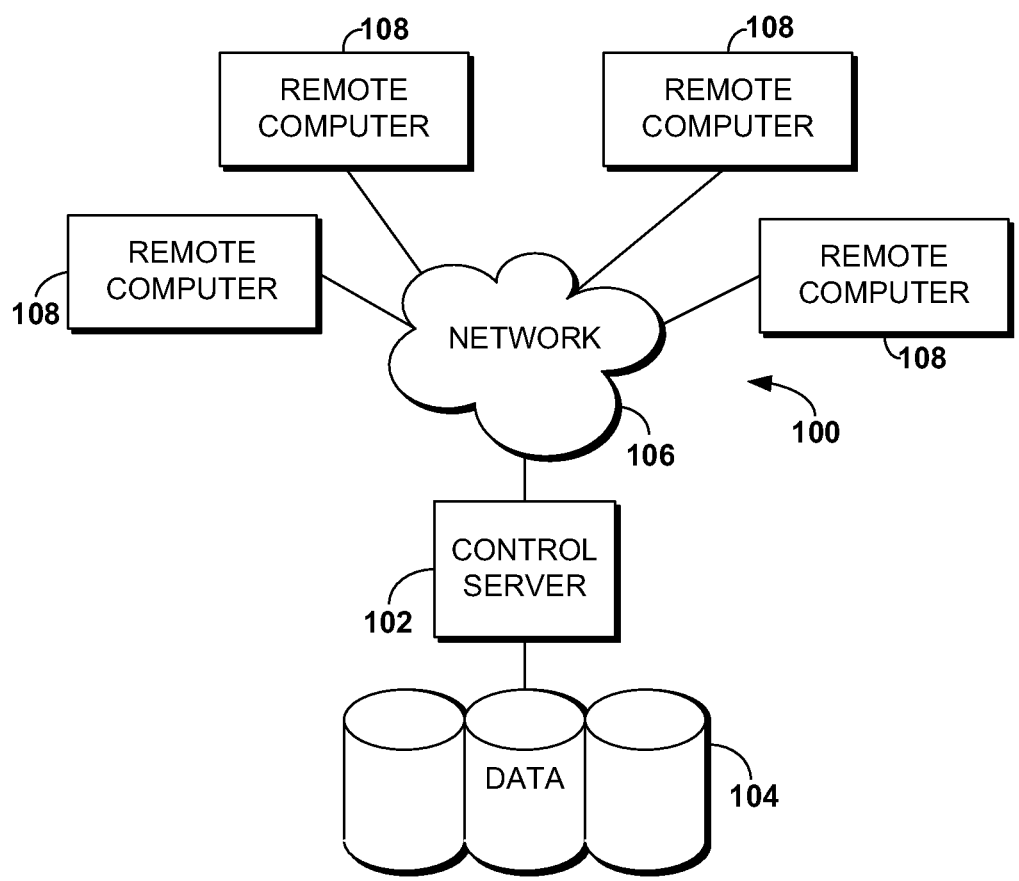
FIG. 1 is a block diagram of an exemplary computing environment suitable for use in implementing the present invention.

Referring now to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary computing system environment 100 includes a general purpose computing device in the form of a control server 102. Components of the control server 102 may include, without limitation, a processing unit, internal system memory, and a suitable system bus for coupling various system components, including database cluster 104, with the control server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and non-volatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the control server 102. The control server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, mobile devices, servers, routers, network PCs, peer devices, other common network nodes, or the like, and may include some or all of the components described above in relation to the control server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the control server 102 may include a modem or other means for establishing communications over the WAN, such as the Internet. In a networked environment, program modules or portions thereof may be stored in the control server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the control server 102 or convey the commands and information to the control server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 102. In addition to a monitor, the control server 102 and/or remote computers 108 may include other peripheral output devices, such as speakers and a printer.

Although many other internal components of the control server 102 and the remote computers 108 are not shown, those of ordinary skill in the art will appreciate that such components and their interconnections are well known. Accordingly, additional details concerning the internal construction of the control server 102 and the remote computers 108 are not further disclosed herein.

Figure 2:
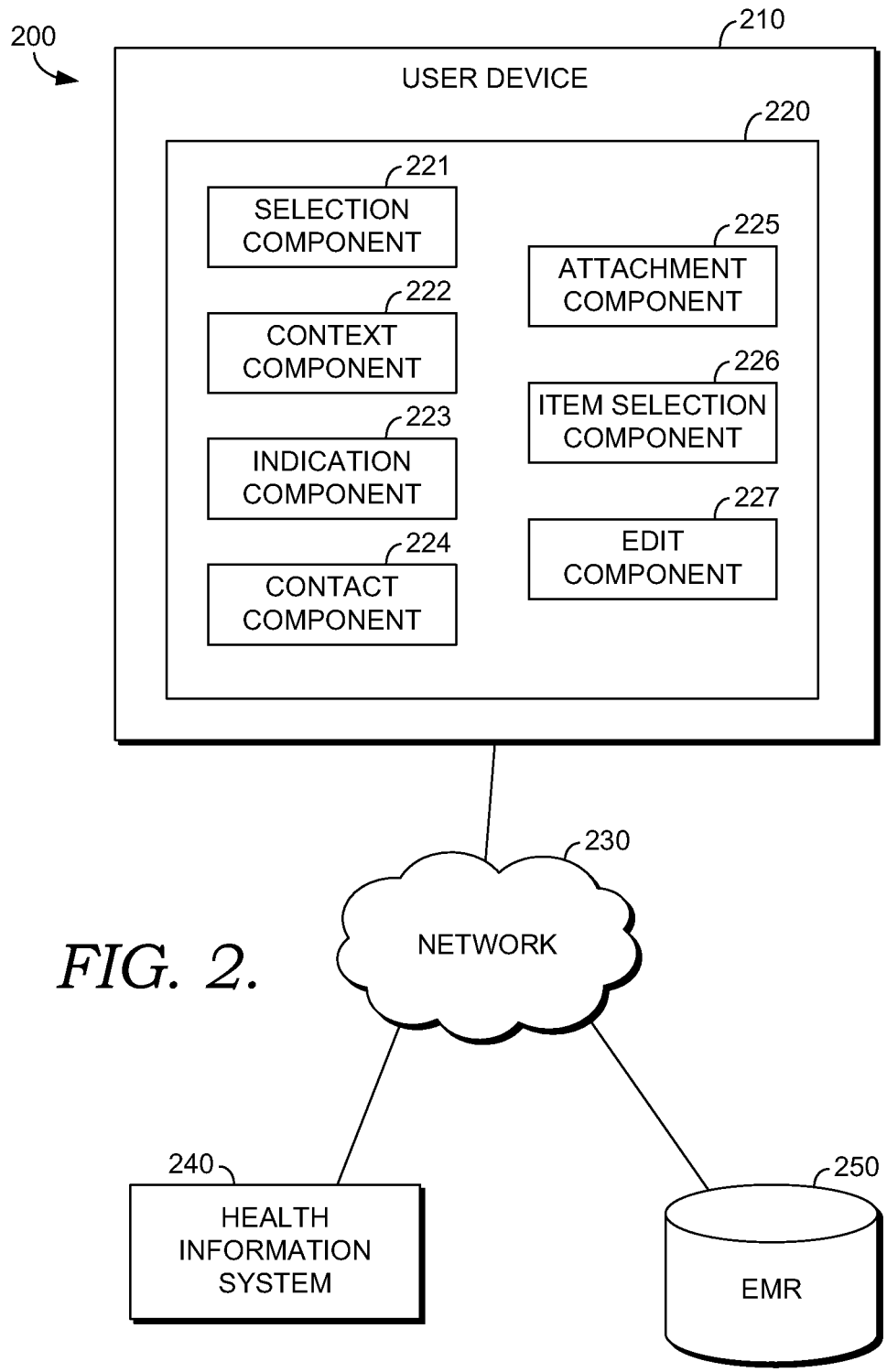
FIG. 2 is a block diagram of an exemplary system for declining, attaching, or editing patient context to mobile voice communication, in accordance with embodiments of the present invention.

With reference to FIG. 2, a block diagram is illustrated that shows an exemplary computing system architecture for implementing embodiments of the present invention. It will be appreciated that the computing system architecture shown in FIG. 2 is merely an example of one suitable computing system and is not intended as having any dependency or requirement related to any single module/component or combination of modules/components.

The computing system 200 includes one or more user devices 210 (e.g., a mobile communication device), context engine 220, network 230, health information system 240, and EMR 250. As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); evidence-based recommendations for specific medical conditions; a record of appointments and physician's notes; billing records; and data received from an associated medical device (e.g. alerts).

User device 210 receives and displays data from health information system 240 and EMR 250 and communicates or otherwise makes the data available to context engine 220. User device 210 also allows a clinician to make voice communication calls, such as, for example, to other clinicians. Although health information system 240 and EMR 250 are illustrated in FIG. 2 as separate components of computing system 200, it should be appreciated that one or more of these components may be included in a single computing device.

Context engine 220 may reside on one or more computing devices, such as, for example, the control server 102 described above with reference to FIG. 1, user device 210, as shown in FIG. 2, or health information system 240. By way of example, the control server 102 includes a computer processor and may be a server, personal computer, desktop computer, laptop computer, handheld device, mobile device, consumer electronic device, or the like. Context engine 220 comprises, in various embodiments, selection component 221, context component 222, indication component 223, contact component 224, attachment component 225, item selection component 226, and edit component 227.

In one embodiment, selection component 221 receives a selection of one an alert from an alert list or one or more patients from a patient list. As described above, the alert list and the patient list are communicated from health information system 240 and/or EMR 250 via to the network to the user device 210 where the data is communicated to or otherwise shared with context engine 220. In various embodiments, the data is associated with alerts and/or one or more patients. These alerts and/or one or more patients may be organized in an alert list and a patient list, respectively. A first clinician may desire to discuss an alert or one or more patients with a second clinician. Accordingly, selection component 221 receives the selection made by the first clinician.

In one embodiment, context component 222 provides context associated with the alert, the one or more patients, or a combination thereof. The context may include the alert or patient demographic information. The context may further include additional information associated with the alert or patient demographic information, such as information received from health information system 240 or EMR 250. The additional information may include protocols, encounter details, patient demographics, care team information, family contacts, insurance information, pharmacy information, and the like. The context provides the clinician with information associated with the selected alert or patient demographic information that can be attached to a call history associated with mobile voice communication for later use.

In one embodiment, indication component 223 receives an indication that the first clinician is initiating voice communication with a second clinician. The indication may be made by pressing a button or activating or triggering the phone (e.g., touch-activated screen, voice command, and the like) on the user device 210. Upon receiving the indication, the first clinician must select the recipient of the voice communication, or in this case, the second clinician. Contact component 224 receives a selection of the second clinician from a contact list. The contact list may be a list displayed on the user device 210 or may be contacts maintained by user device 210 or health information system 240. Or the contact list may merely be a telephone number associated with the second clinician that is selected by the first clinician. The selection may be made by the first clinician selecting the second clinician from a contact list or call history displayed on the user device 210, by voice command, or by manually dialing the telephone number associated with the second clinician.

Once the contact is selected, in one embodiment, attachment component 225 attaches the context to a call history associated with the voice communication. The call history may be available on the user device 210, or a device associated with the second clinician. Further, the call history may be communicated to medical information system 240 and/or stored in the EMR 250. For clarity, the call history may be an item in the call history log of the user device that is associated with the voice communication between the first clinician and the second clinician.

In one embodiment, item selection component 226 receives a selection of an item from a call history associated with voice communication. For example, an item within the call history on user device 210 may be associated with a voice communication that did not have, or had incomplete or incorrect context attached to it. The clinician may be reviewing items in the call history and determine that context should be added, edited, or declined for a particular item. The clinician makes the appropriate selection and item selection component 226 receives the selection accordingly.

In one embodiment, edit component 227 receives a selection to decline, attach, or edit context associated with the item. Edit component 227 may cause a pop-up to appear, allowing the clinician to select an appropriate action. After the clinician selects the item from the call history, the clinician selects the appropriate action. For example, the clinician may just want to indicate that no context is necessary and selects to decline context. Or the clinician may determine that additional or different detail is necessary and selects to edit context. Or the clinician may determine that no context was attached and the item would provide later benefits if context were attached. In this example, the clinician selects to attach context.

In one embodiment, context selection component 221, upon receiving the selection to attach or edit context, receives a selection of the context to add or edit for the item. The context comprises an alert, one or more patients, or a combination thereof. This allows the clinician to select an alert, one or more patients (e.g., a first clinician discusses multiple patients with a second clinician), or a combination thereof to attach or edit for the item in the call history. In one embodiment, attach component 225 attaches or edits the context associated with the item in accordance with the selection of the context.

Figure 3:
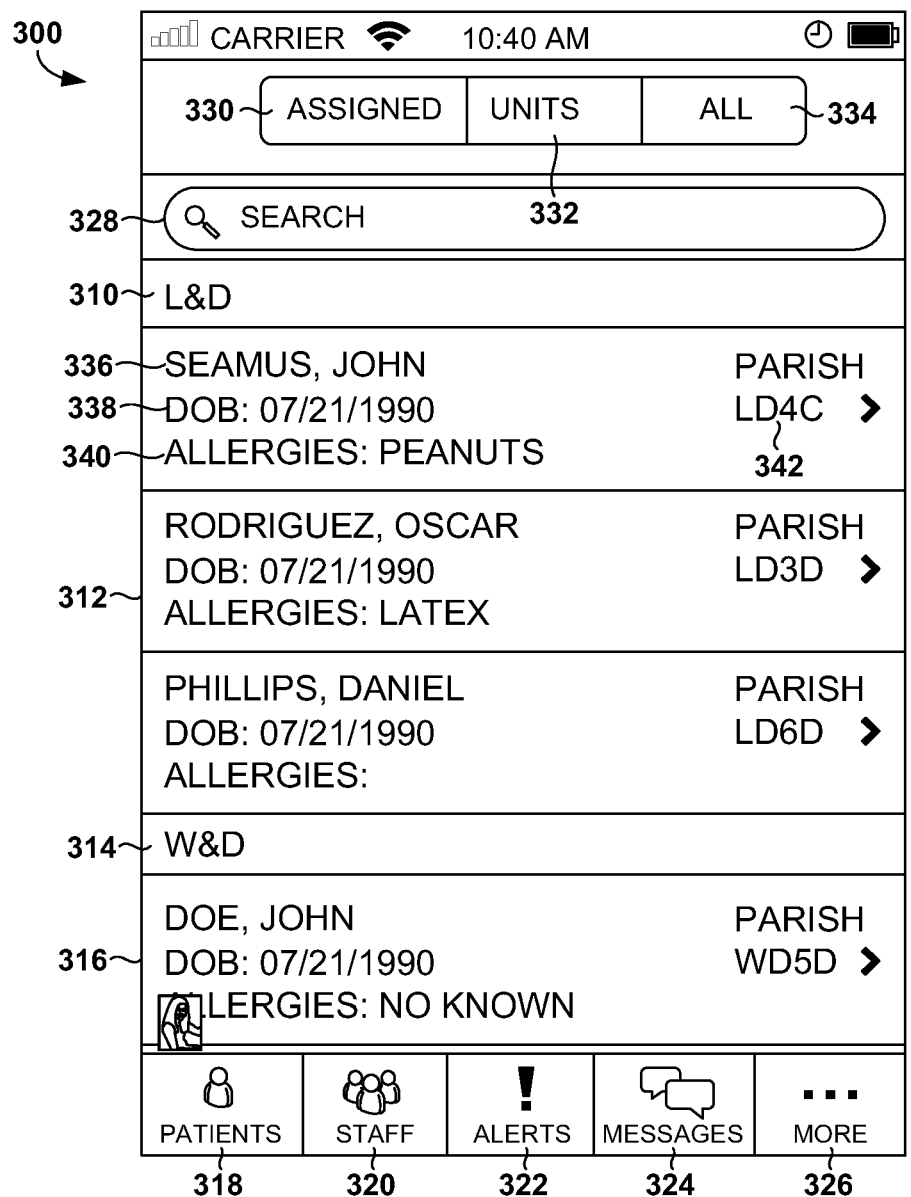
FIGS. 3-19 are illustrative graphical user interface displays of declining, attaching, or editing patient context to mobile voice communication, in accordance with embodiments of the present invention.

Referring now to FIG. 3, an illustrative screen display depicts list display area 400 that displays a patient list, in accordance with embodiments of the present invention. List display area includes a search bar 328 to search for a particular patient. List display area also includes unit organizers 310, 314 for organizing the patient list by unit. List display are also includes demographic bar 312, 316 that displays context associated with a particular patient. Context includes patient name 336, date of birth 338, allergies 340, and location 342. List display area further includes tabs 330, 332, 334 for displaying particular patients of a healthcare facility. For example, assigned tab 430 includes in the patient list patients that are assigned to the clinician using the mobile device. Units tab 332 includes in the patient list patients organized by unit (as depicted in FIG. 3). All tab 334 includes all patients in the patient list. List display area 300 also includes buttons 318, 320, 322, 324, 326 for displaying additional items. For example, patients button 318 displays a patient list in the list display area 300. Staff button 320 displays a staff list in the list display area 300. Alerts button 322 displays an alert list in the list display area 300. Messages button 324 displays a message list in the list display area 300. More button 326 displays other list topics that can be displayed in the list display area 300. As can be appreciated, other list topics can include any health care related topic that may be useful to a clinician utilizing a mobile device in a healthcare facility.

Figure 4:
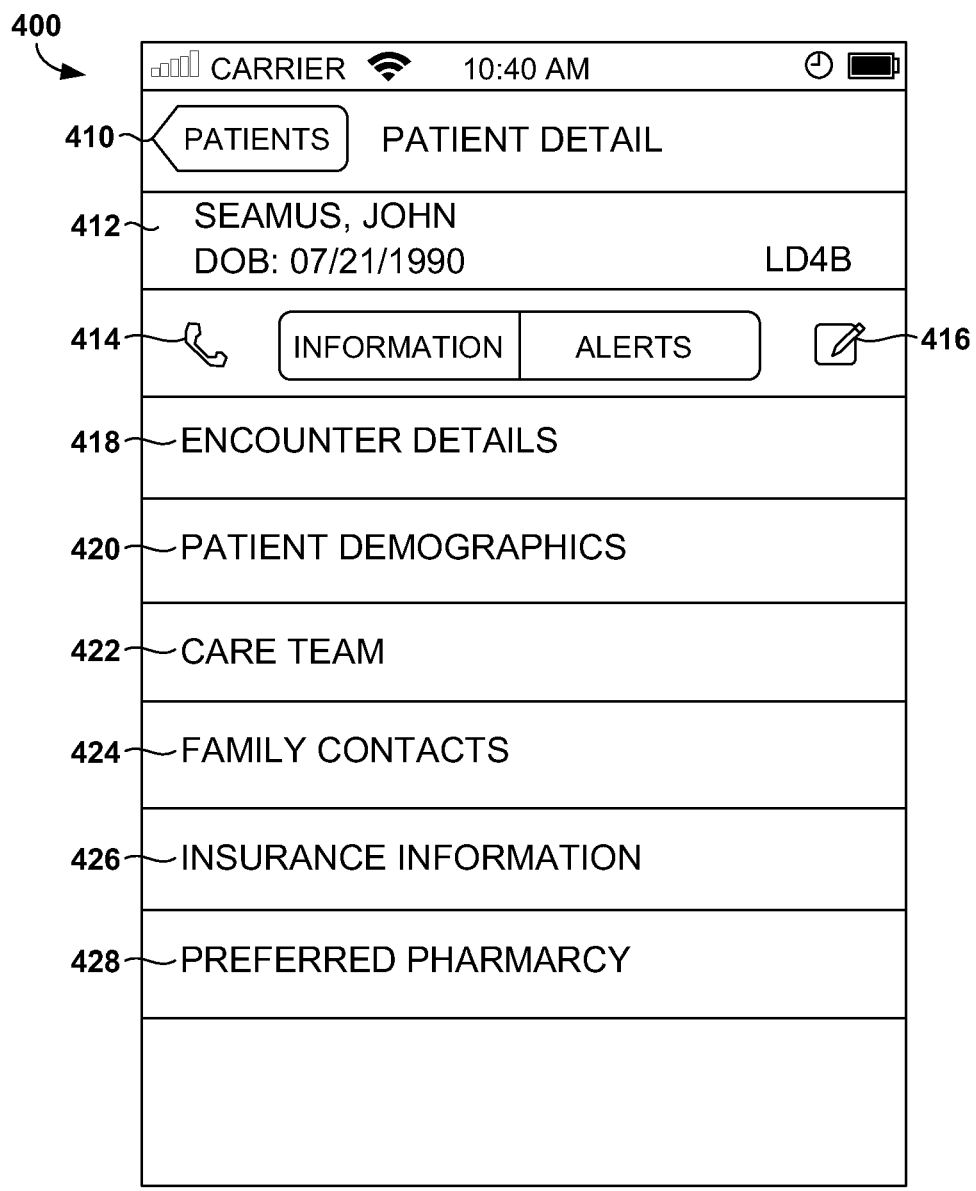

Referring now to FIG. 4, illustrative screen display depicts context display area 400, in accordance with embodiments of the present invention. Context display area 400 displays context associated with an alert, one or more patients, or a combination thereof. Context display area 400 may be utilized to select the desired context to add to a call history associated with voice communication. For example, a first clinician may desire to discuss a particular topic with a second clinician regarding a patient. In order to record the topic of discussion to the EMR, the first clinician selects the appropriate topic from context display area 400. Context display area 400 allows the first clinician to review or select as detailed or general information as desired. For example, context display area 400 includes patient information 412, encounter details 418, patient demographics 420, care team 422, family contacts 424, insurance information 426, and preferred pharmacy 428. Call display area 414 displays an indicator for initiating a voice communication. Once the desired information is reviewed and/or selected, the first clinician can select the indicator from call display area 414 or the text message button 416. The first clinician can return to list display area 300 by selecting the patients button 410.

Figure 5:
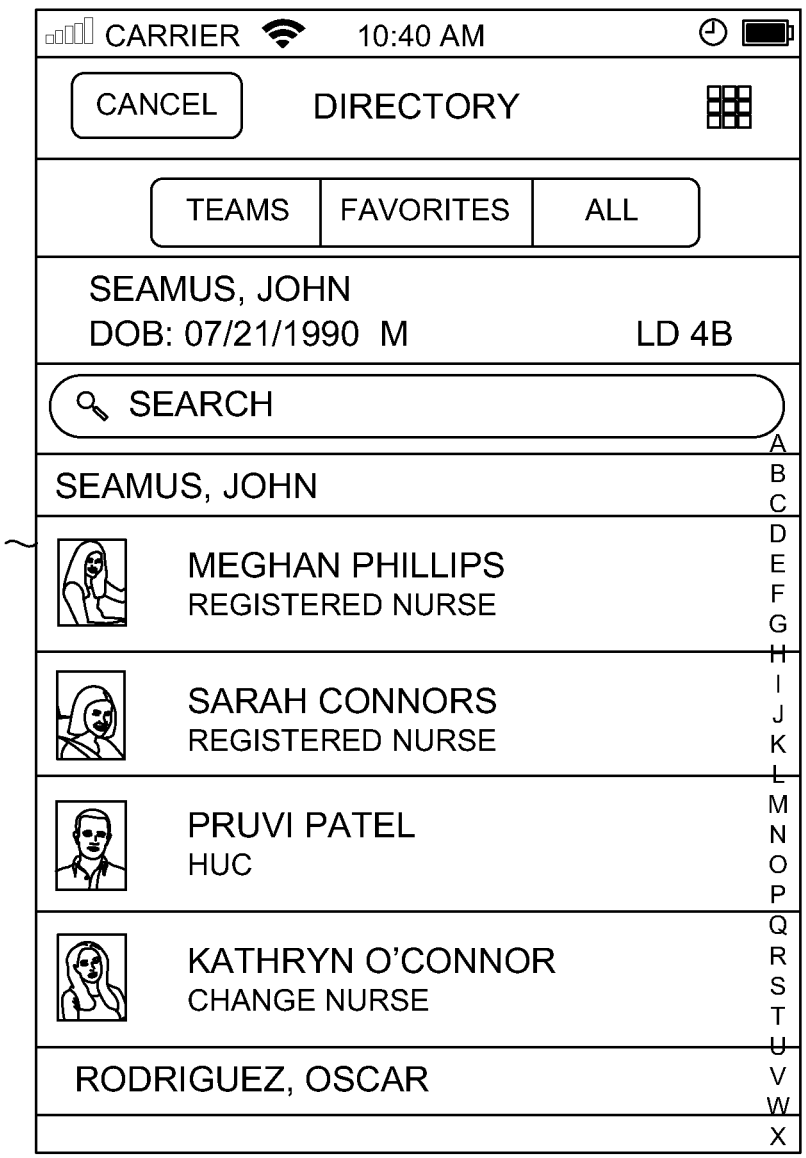

Referring now to FIG. 5, an illustrative screen display depicts a contact display area 510, in accordance with an embodiment of the present invention. As mentioned above, the first clinician may desire to view, select, or communicate (e.g., call or text message) a member of the care team for a particular patient. By selecting either the care team 522, call display area 514, or text message button 516 causes a contact list to be displayed in the contact display area 510 on the first clinician's mobile device.

Figure 6:
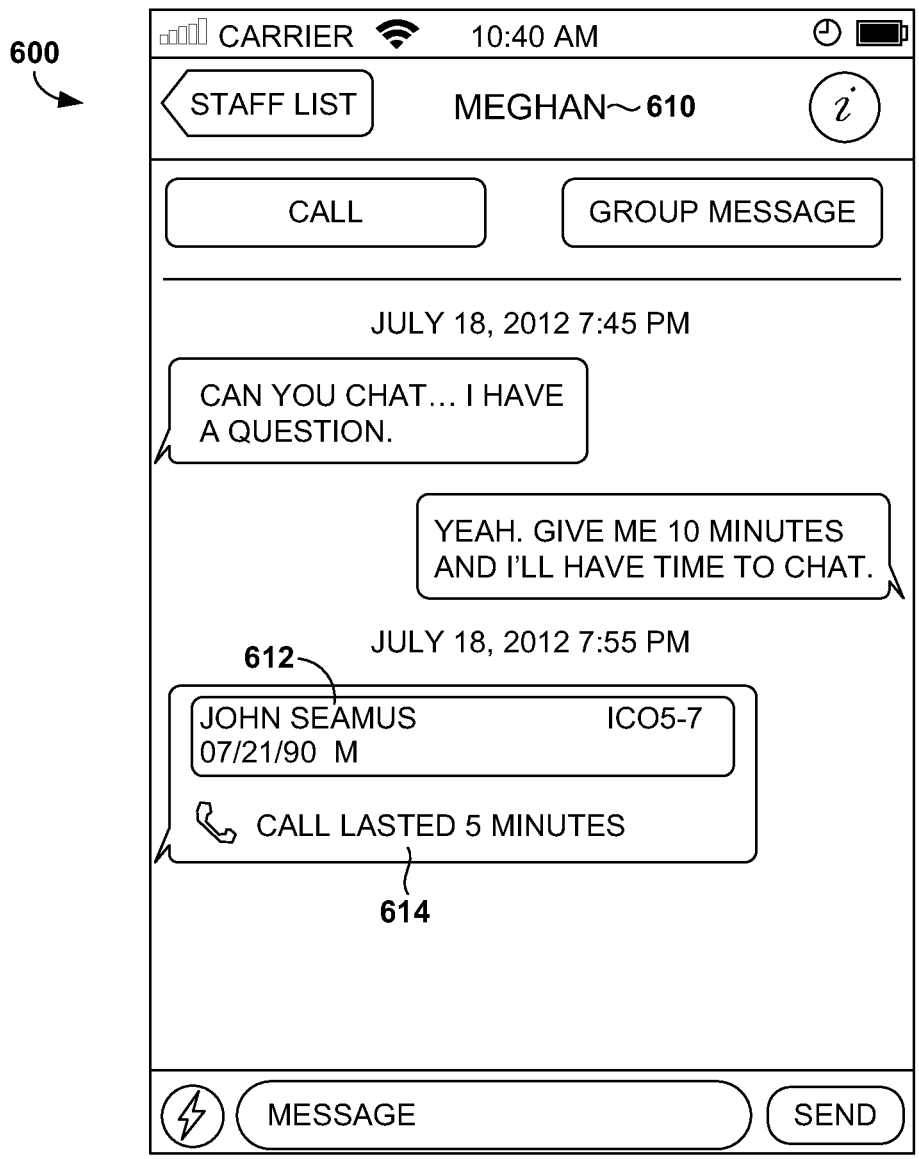

Referring now to FIG. 6, illustrative screen display depicts call history display area 600, in accordance with embodiments of the present invention. Call history display area 600 displays a call history or message history associated with a mobile device for a clinician. Attachment display area 612 displays the context attached to the call history 614 associated with the voice communication.

Figure 7:
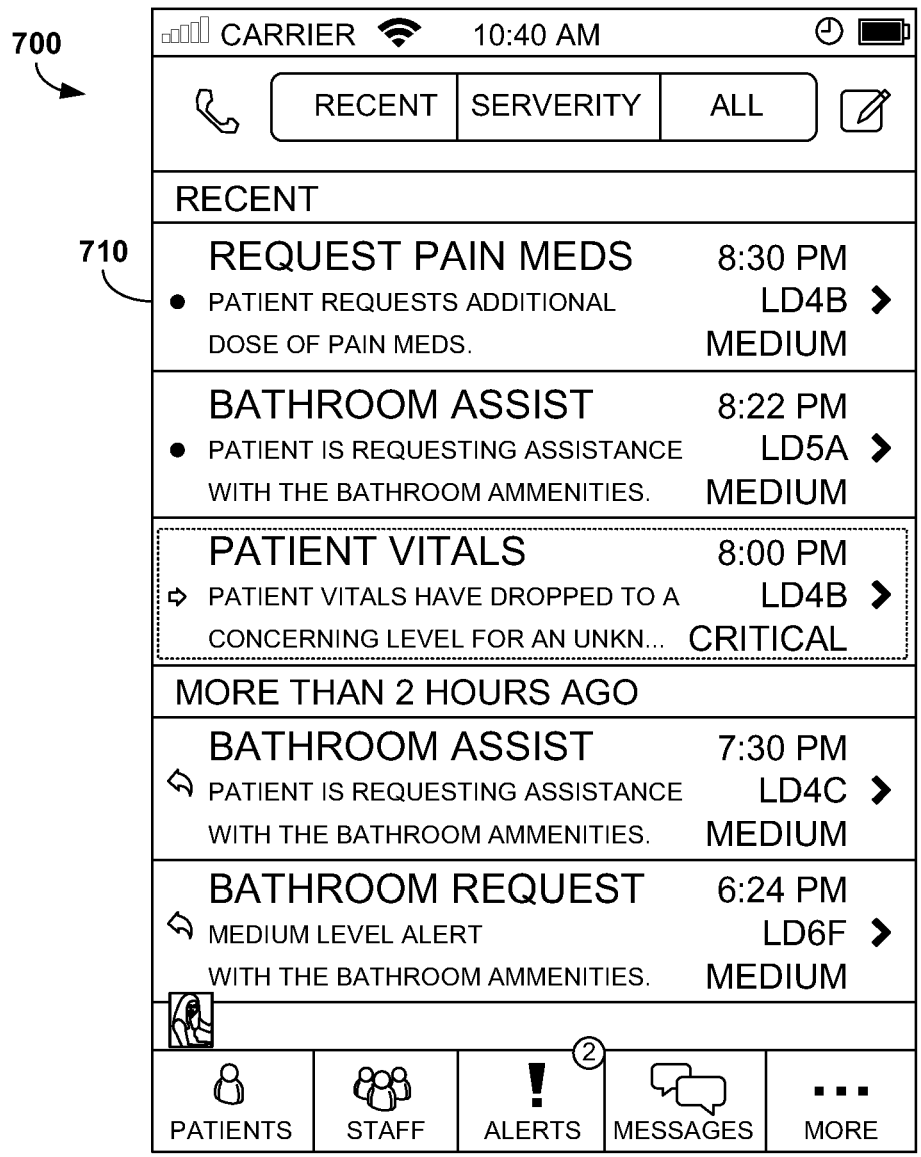

Referring now to FIG. 7, an illustrative screen display depicts list display area 700 that displays an alert list, in accordance with embodiments of the present invention. List display area 700 includes tabs for displaying alerts by category. For example, alerts can be displayed according to a timeframe, such as recent 710, or by severity. Or, all alerts related to a unit, a clinician, or a facility can be displayed.

Figure 8:
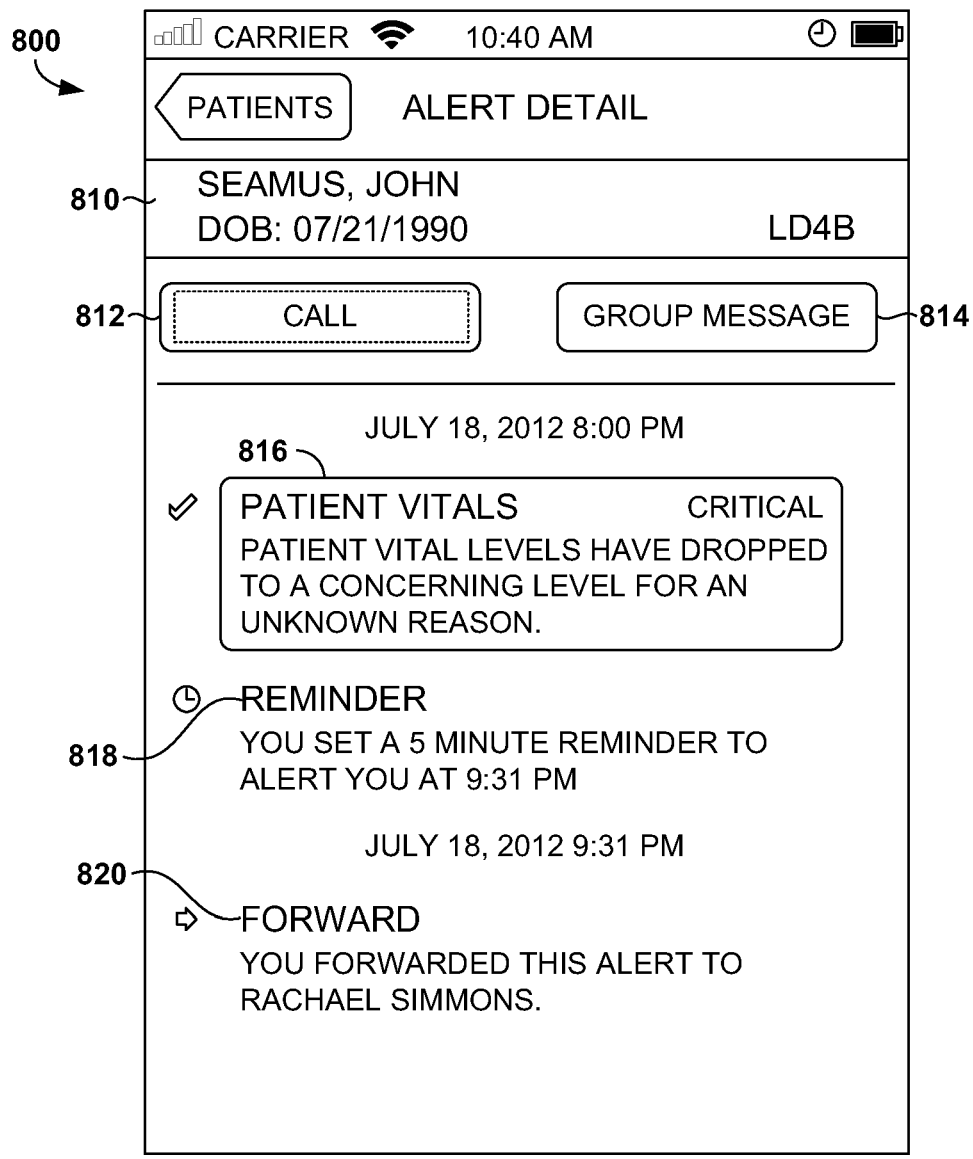

Referring now to FIG. 8, an illustrative screen display depicts context display area 800, in accordance with embodiments of the present invention. Context display area 800 displays context associated with an alert, one or more patients, or a combination thereof. Context display area includes patient information 810. Context display area 800 includes alert details 816, reminders 818, and communication history 820. Call display area 812 displays an indicator for initiating a voice communication. Once the desired information is reviewed and/or selected, the first clinician can select the indicator from call display area 812 or the group message button 814. The first clinician can return to list display area 800 by selecting the patients button.

Figure 9:
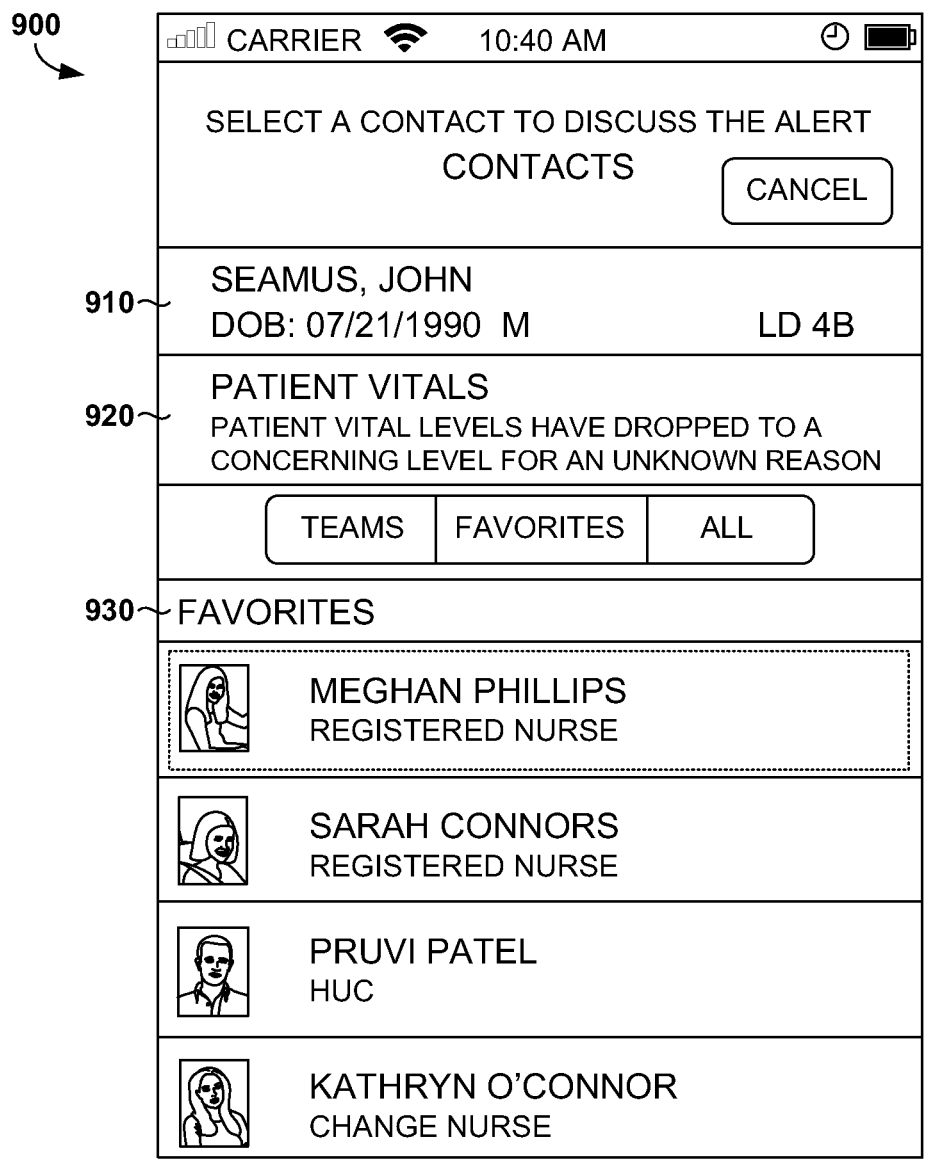

Referring now to FIG. 9, an illustrative screen display depicts a contact display area 900, in accordance with an embodiment of the present invention. As mentioned above, the first clinician may desire to communicate (e.g., call or text message) a member of the care team for a particular patient. By selecting either the call display area 912 or group message button 914 causes a contact list to be displayed in the contact display area 900 on the first clinician's mobile device. Contact display area includes patient information 910, alert information 920, and a list of selectable or favorite contacts 930.

Figure 10:
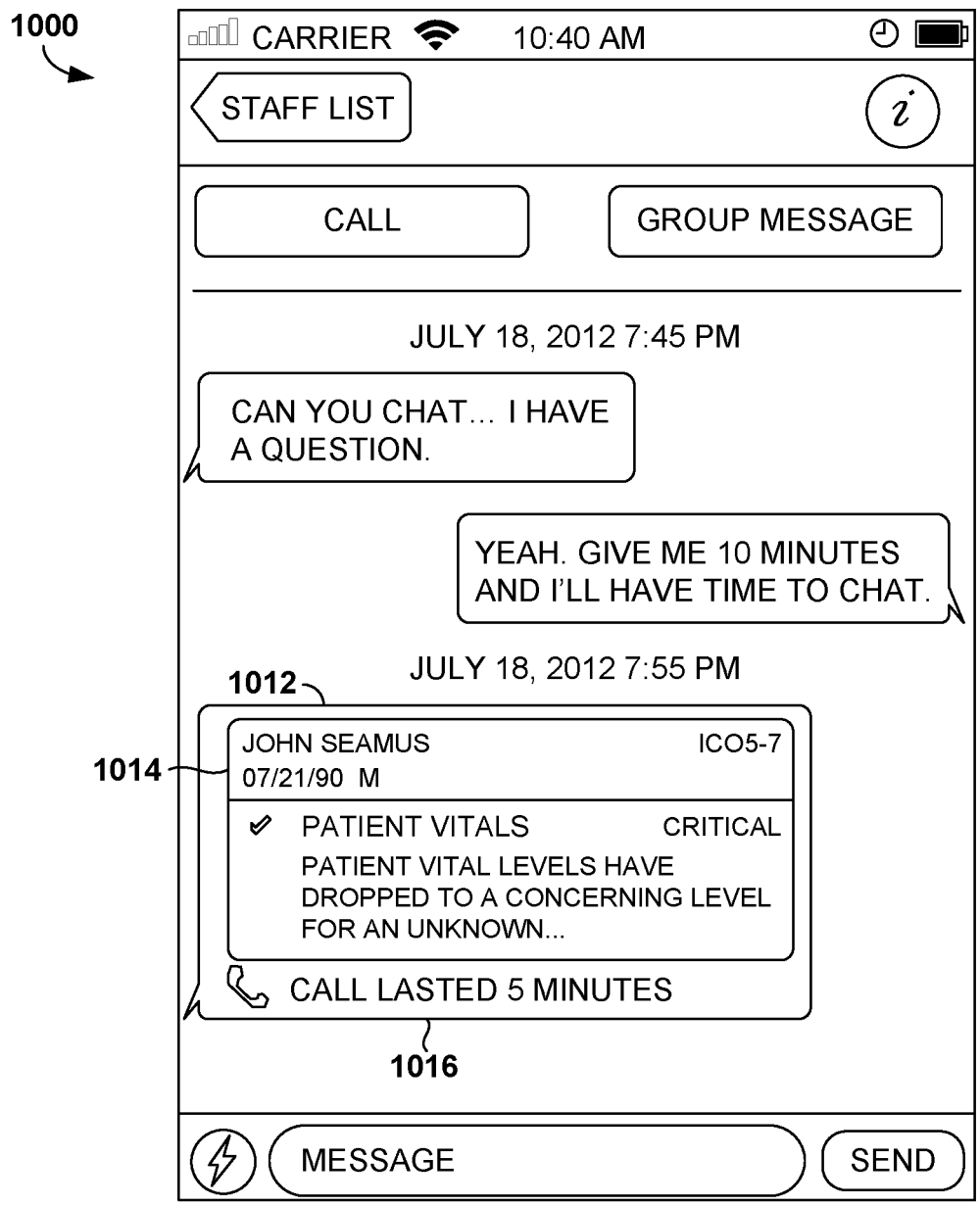

Referring now to FIG. 10, illustrative screen display depicts call history display area 1000, in accordance with embodiments of the present invention. Call history display area 1000 displays a call history or message history associated with a mobile device for a clinician 1010. Attachment display area 1012 displays the context 1014 attached to the call history 1016 associated with the voice communication.

Figure 11:
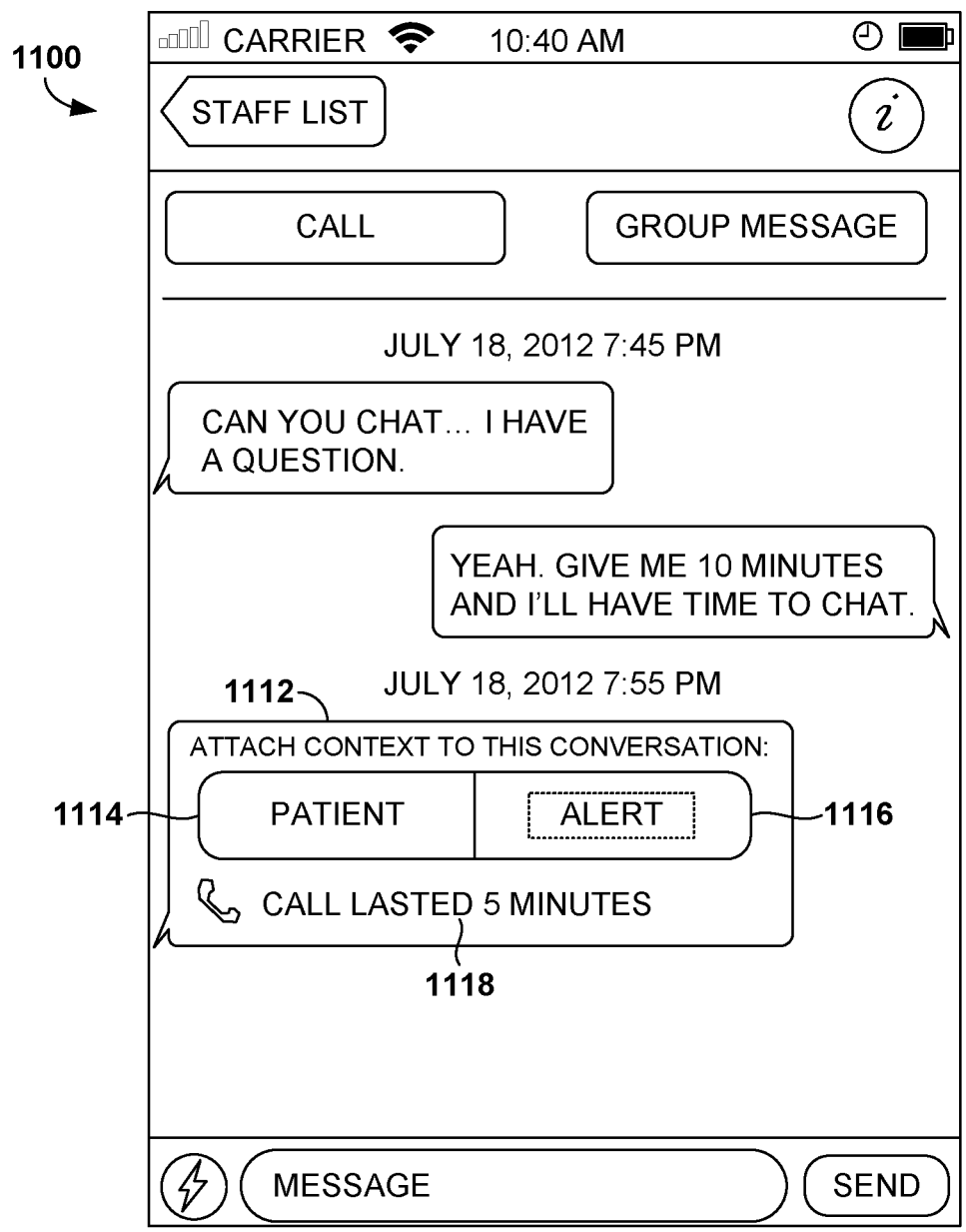

Referring now to FIG. 11, an illustrative screen display depicts a call history display area 1100, in accordance with embodiments of the present invention. Call history display area 1100 includes history associated with voice communication and/or text message communication. Item display area 1112 further displays a patient button 1114 and an alert button 1116 for a particular item 1118 in the call history. The clinician 1110 may desire to select either the patient button 1114 or the alert button 1116 to add the desired context to the particular item 1118.

Figure 12:
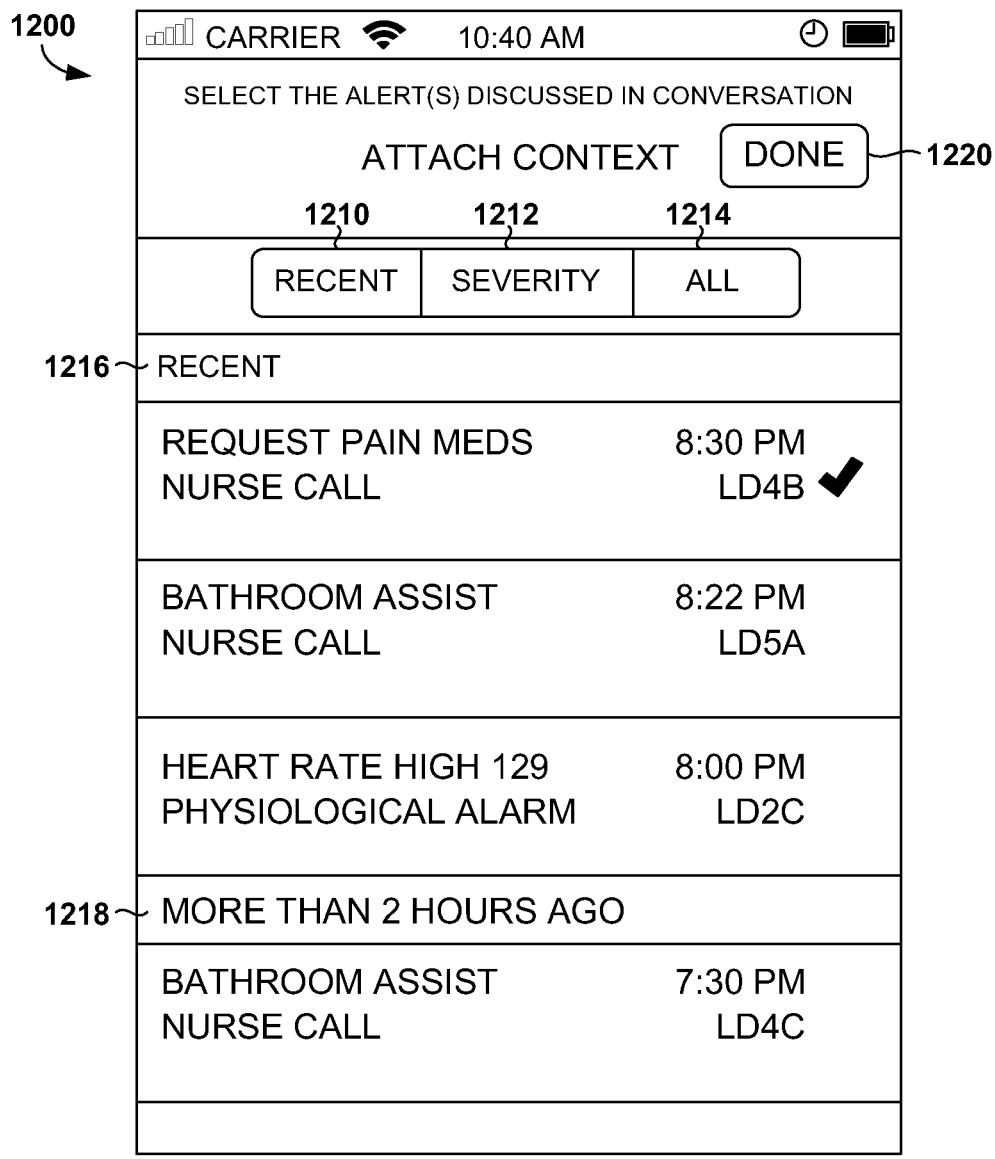

Referring now to FIG. 12, an illustrative screen display depicts a list display area 1200, in accordance with embodiments of the present invention. List display area includes tabs 1210, 1212, 1214 for displaying alerts by category. For example, alerts can be displayed according to a timeframe, such as most recent 1210, by severity 1212. Or, all 1214 alerts related to a unit, a clinician, or a facility can be displayed. Lists 1216, 1218 based on the category are displayed. Once the desired alert is selected, a done button 1220 allows the context to be attached to the particular item in the call history.

Figure 13:
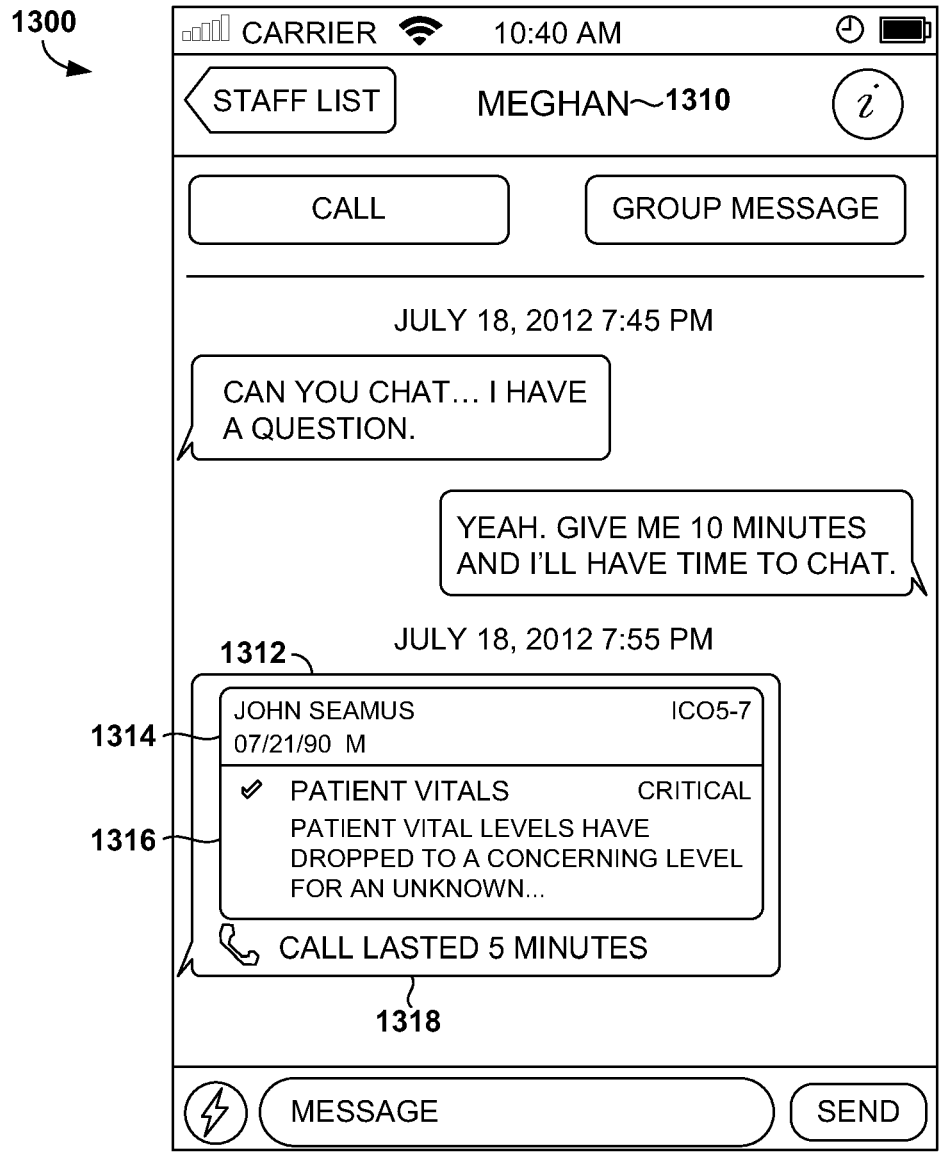

Referring now to FIG. 13, an illustrative screen display depicts call history display area 1300, in accordance with embodiments of the present invention. Call history display area 1300 displays a call history or message history associated with communication with another clinician 1310. Attachment display area 1312 displays the context 1314, 1316 attached to the call history 1318 associated with the voice communication.

Figure 14:
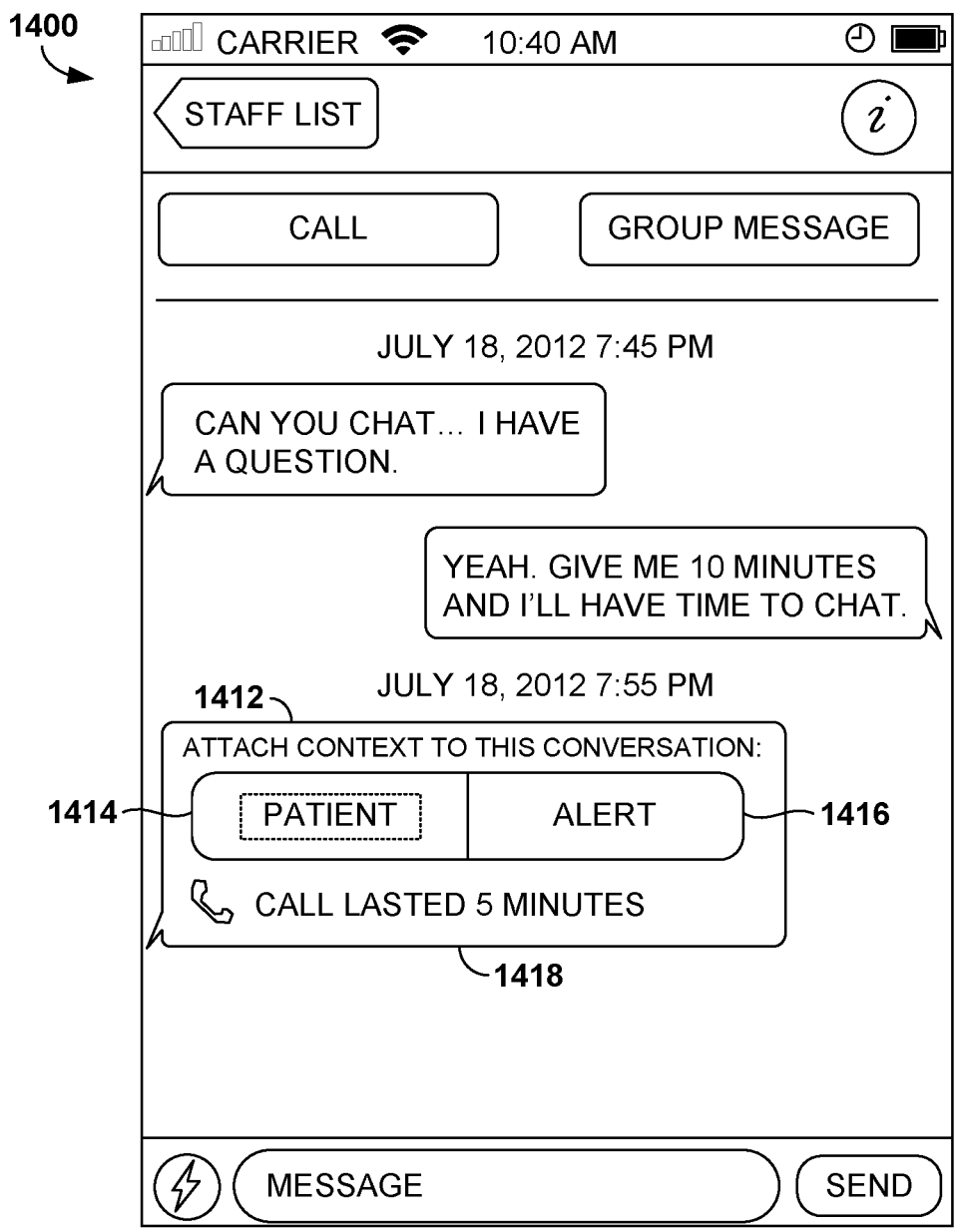

Referring now to FIG. 14, an illustrative screen display depicts a call history display area 1400, in accordance with embodiments of the present invention. Call history display area 1400 includes history associated with voice communication and/or text message communication. Item display area 1412 further displays a patient button 1414 and an alert button 1416 for a particular item 1418 in the call history. The clinician 1410 may desire to select either the patient button 1414 or the alert button 1416 to add the desired context to the particular item 1418.

Figure 15:
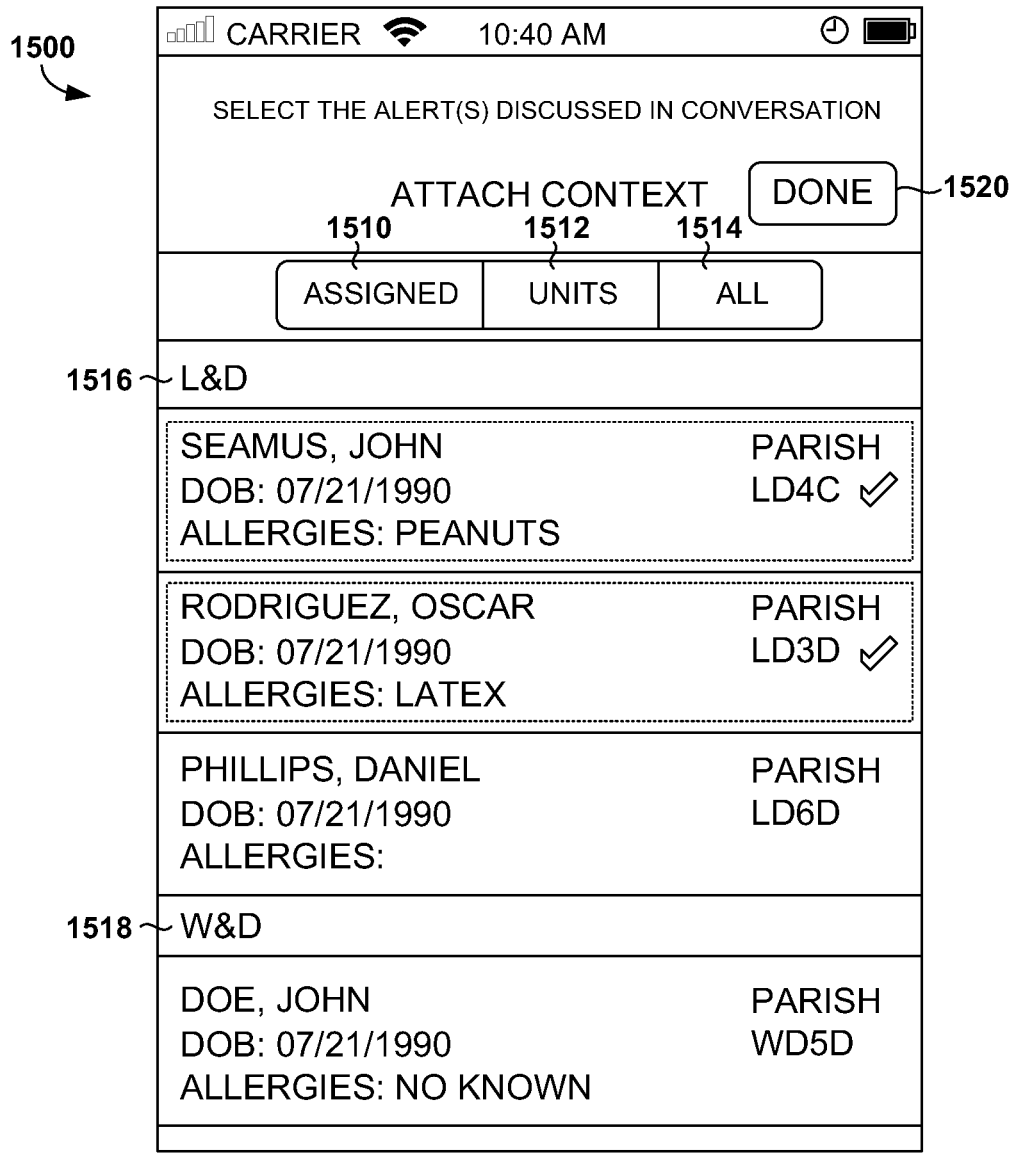

Referring now to FIG. 15, an illustrative screen display depicts a list display area 1500, in accordance with embodiments of the present invention. List display area includes tabs 1510, 1512, 1514 for displaying patients category. For example, patients can be displayed according to assignment 1510, by unit 1512. Or, all 1514 patients for a healthcare facility can be displayed. Lists 1516, 1518 based on the category are displayed. Once the desired patient is selected, a done button 1520 allows the context to be attached to the particular item in the call history.

Figure 16:
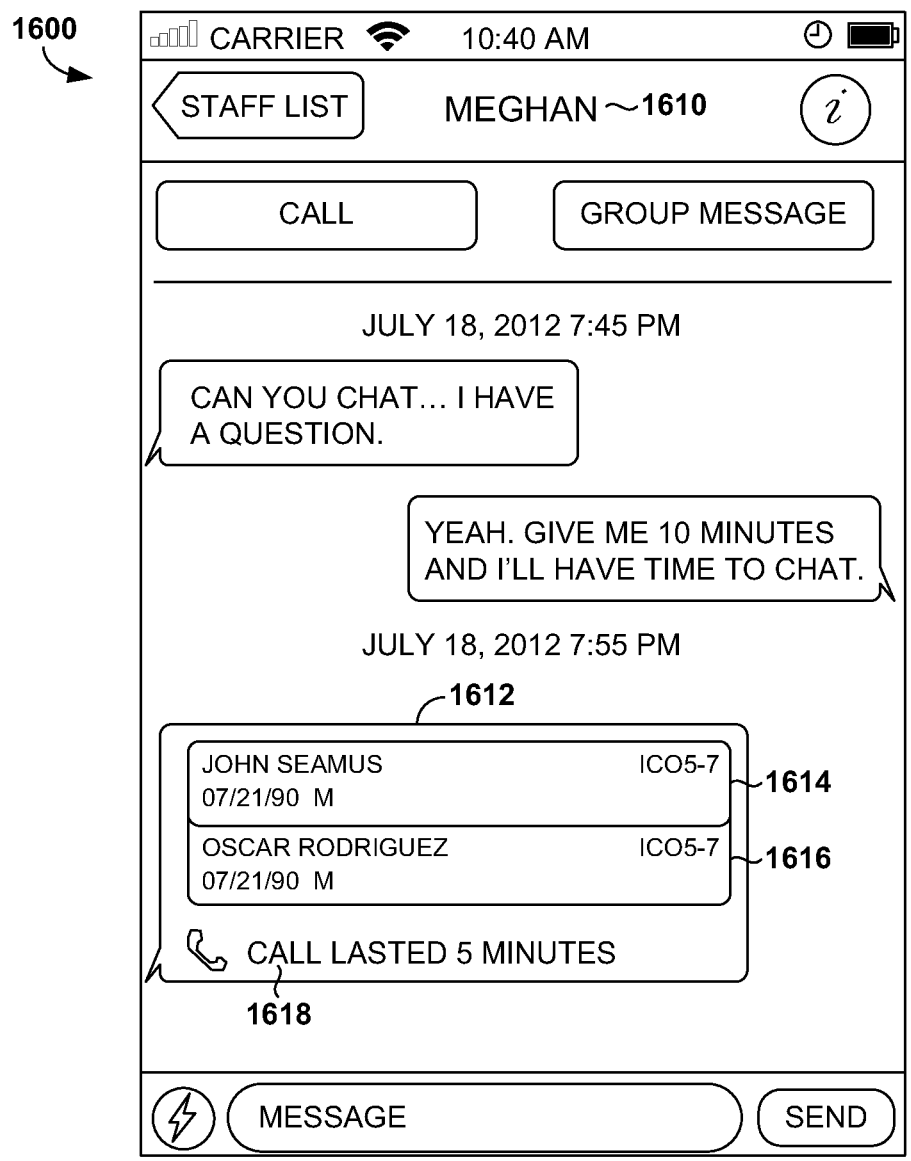

Referring now to FIG. 16, an illustrative screen display depicts call history display area 1600, in accordance with embodiments of the present invention. Call history display area 1600 displays a call history or message history associated with communication with another clinician 1610. Attachment display area 1612 displays the context 1614, 1616 attached to the call history 1618 associated with the voice communication.

Figure 17:
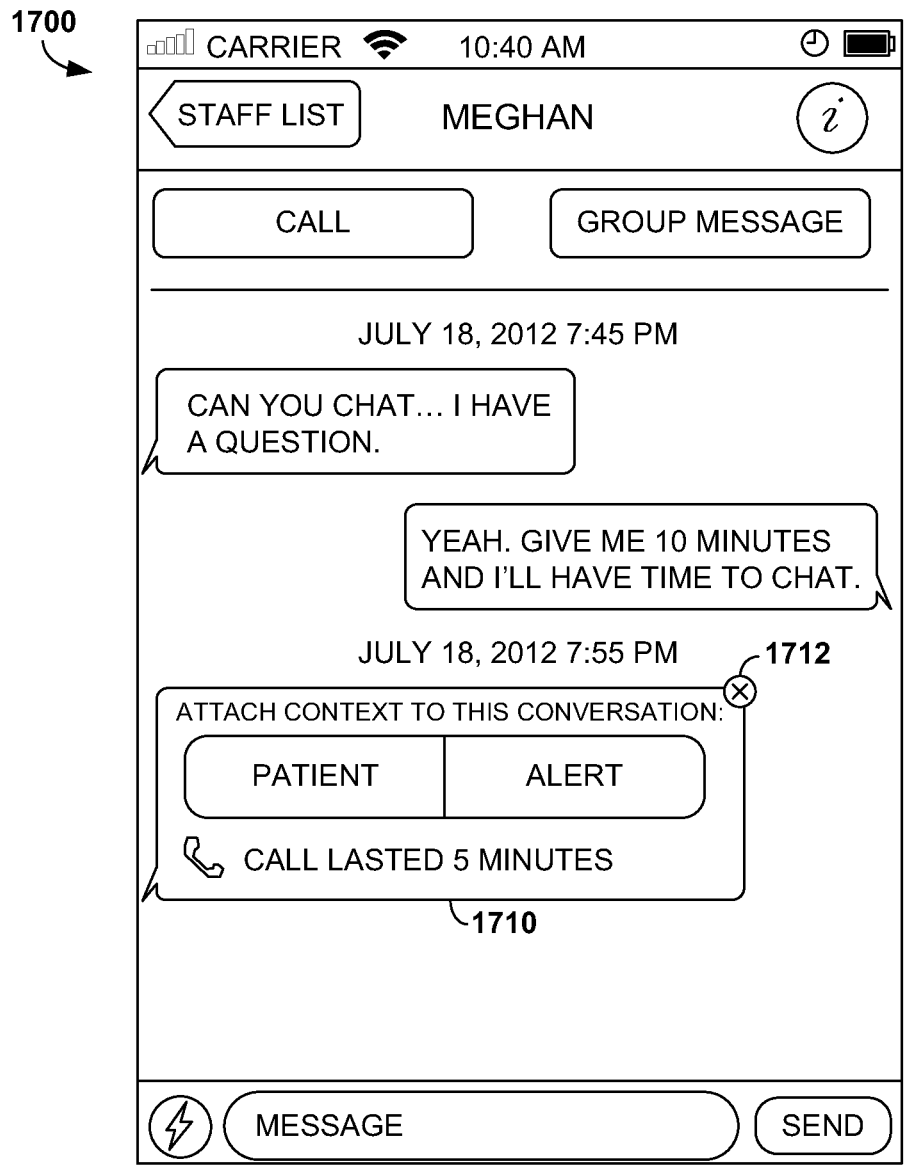

Referring now to FIG. 17, an illustrative screen display depicts a call history display area 1700 and a selection display area 1712, in accordance with embodiments of the present invention. Call history display area 1700 displays a call history associated with voice communication. Selection display area 1712 displays an indicator for selecting to decline context to an item 1710 associated with the call history. Selecting to decline context to the item 1710 results in the display merely displaying the length of the communication, rather than including buttons for attaching context to the item.

Figure 18:
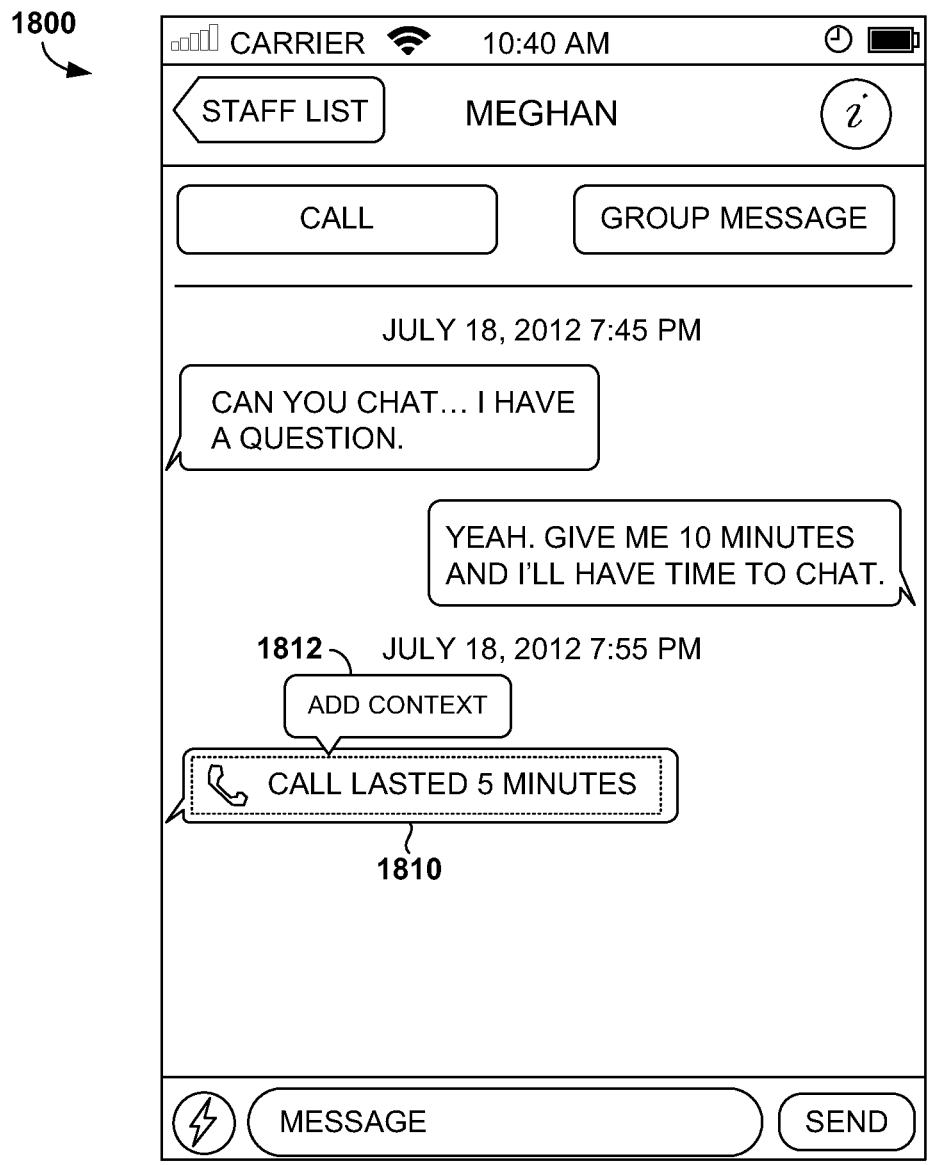

Referring now to FIG. 18, an illustrative screen display depicts a call history display area 1800 and a selection display area 1812, in accordance with embodiments of the present invention. Call history display area 1800 displays a call history associated with voice communication. Selection display area 1812 displays an indicator for selecting to attach context to an item 1810 associated with the call history. Selecting to attach context to the item 1810 results allows the user to attach context to the item, as described herein. Upon selecting to attach context to the item 1810 displays a context area that displays context comprising an alert, one or more patients, or a combination thereof to associated with the item (as described herein).

Figure 19:
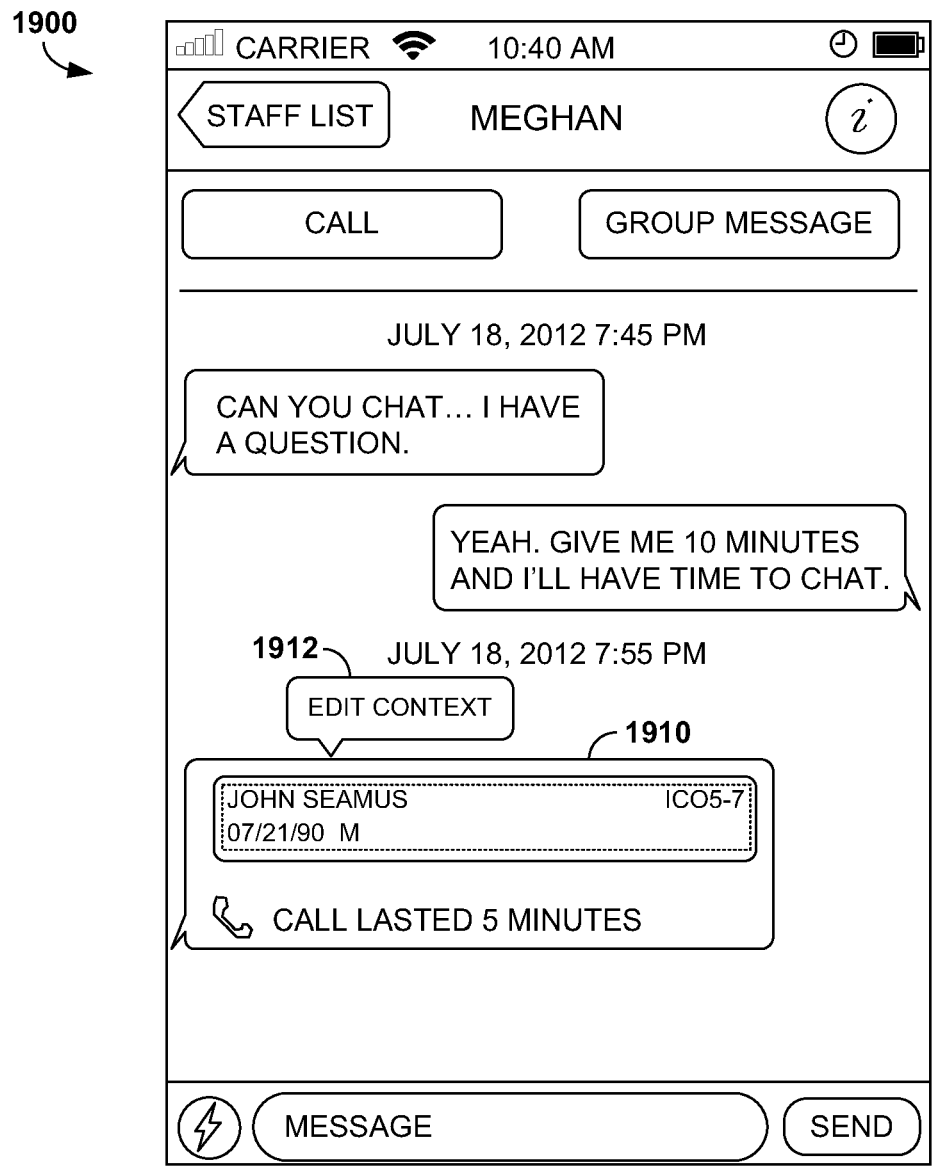

Referring now to FIG. 19, an illustrative screen display depicts a call history display area 1900, a selection display area 1912, and attachment display area in accordance with embodiments of the present invention. Call history display area 1900 displays a call history associated with voice communication. Selection display area displays an indicator for selecting to edit context to an item 1910 associated with the call history. Selecting to edit context to the item 1910 allows the user to edit context for the item. Upon selecting to edit context to the item 1910 displays a context area that displays context comprising an alert, one or more patients, or a combination thereof to associated with the item (as described herein for attaching context). Attachment display area displays the context associated with the item in accordance with the selection of content.

Figure 20:
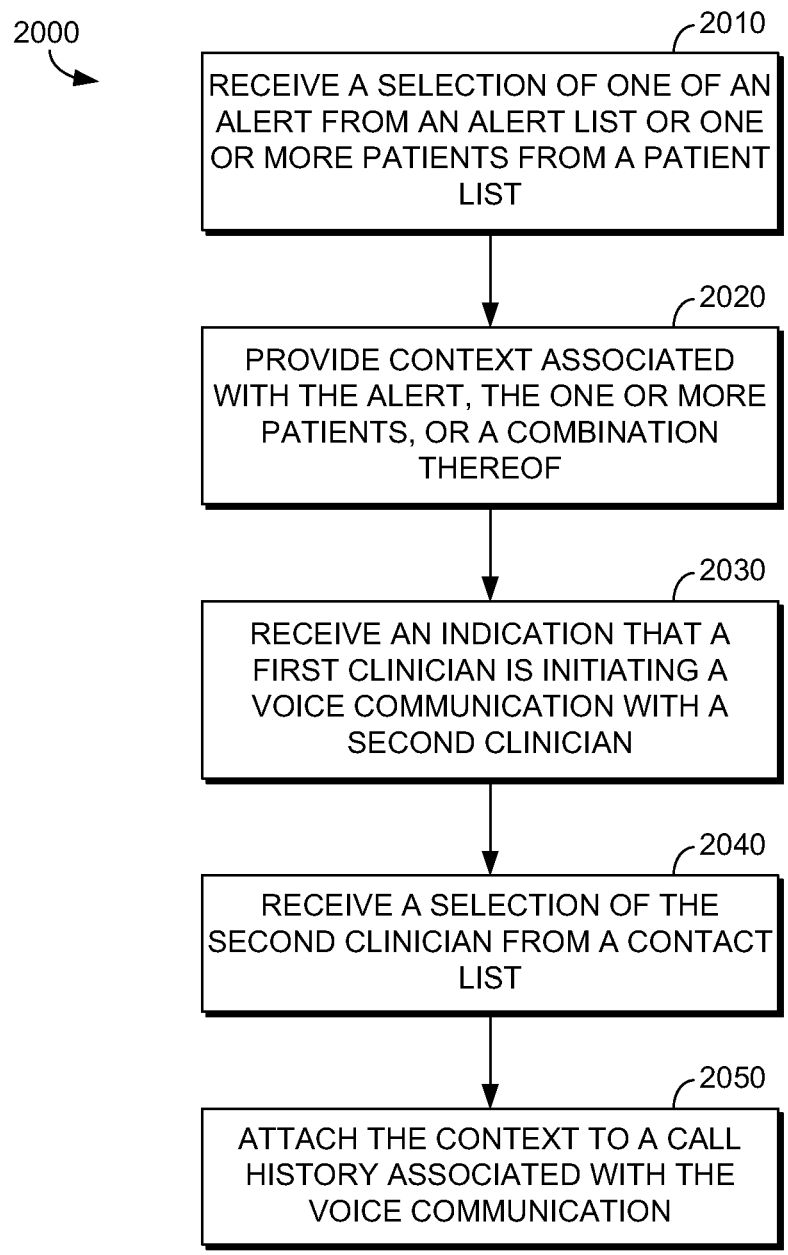
FIG. 20 is a flow diagram showing a method for attaching patient context to mobile voice communication, in accordance with an embodiment of the present invention.

Referring now to FIG. 20, an illustrative flow diagram 2000 is shown of a method for attaching patient context to mobile voice communication, in accordance with embodiments of the present invention. At step 2010, a selection of one of an alert from an alert list or one or more patients from a patient list is received. Context associated with the alert, the one or more patients, or a combination thereof is provided at step 2020. At step 2030, an indication that a first clinician is initiating a voice communication with a second clinician is received. A selection of the second clinician is received, at step 2040, from a contact list. At step 2050, the context is attached to a call history associated with the voice communication. The call history and attached context is stored in the EMR to be used for later purposes. In embodiments, a clinician is able to make a phone call while viewing patient details. When the clinician is viewing a patient's information, the patient's demographic bar is present on the display. This bar indicates that the information the user is viewing is related to the patient. The bar also indicates that patient context is attached to any action made when it is present. Thus, as the clinician makes a phone call or text message from a display that has a demographic bar (i.e., patient detail or alert detail display), the patient context (alert and/or patient information) is included in the message log and stored in the EMR for future analytics.

Figure 21:
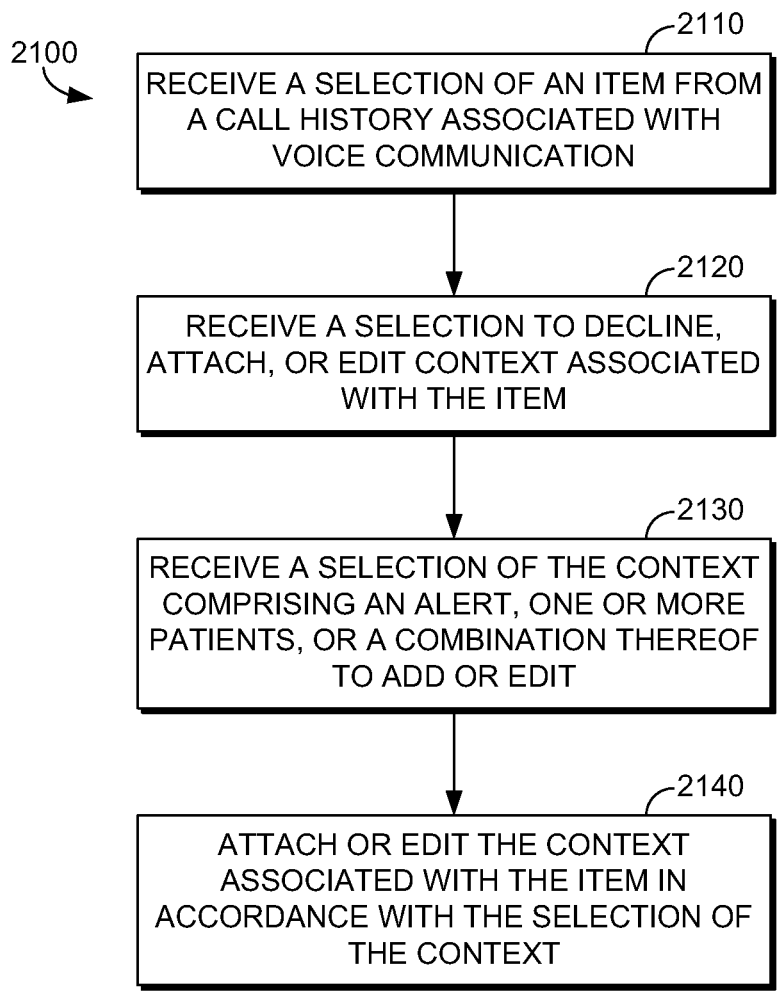
FIG. 21 is a flow diagram showing a method for declining, attaching, or editing patient context to mobile voice communication, in accordance with an embodiment of the present invention.

Referring now to FIG. 21, an illustrative flow diagram 2100 is shown of a method for declining, attaching, or editing patient context to mobile voice communication, in accordance with embodiments of the present invention. At step 2110, a selection of an item from a call history associated with voice communication is received. A selection to decline, attach, or edit context associated with the item is received at step 2120. A selection of the context to attach or edit is received at step 2130. The context comprises an alert, one or more patients, or a combination thereof. At step 2140, the context to be associated with the item is attached or edited in accordance with the selection of the context. When the clinician is not viewing a patient's information while communicating with another clinician, a prompt is provided after the communication is complete. The prompt allows the user to attach patients or alerts (i.e., context) to the communication. By attaching the context to the communication, the clinician is able to include the patient or alert associated with the communication to the message history. The message history, including the context, is stored in the EMR for future analytics.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

Having thus described the invention, what is claimed is:

1. One or more non-transitory computer storage media storing computer-executable instructions that, when executed by a computing device, cause the computing device to perform operations comprising:
receiving, by a device associated with a first clinician, data communicated by a remote server device monitoring a plurality of patients through a network, the data including a patient alert and a plurality of contacts that is populated based on the patient alert;
responsive to selection of the received patient alert, providing for display a contact list including the plurality of contacts via a graphical user interface (GUI) of the device;
responsive to selection of a particular contact from the displayed contact list, initiating a communication with a remote computing device associated with the particular contact;
responsive to a determination that the communication initiated with the remote computing device has terminated, generating a communication log entry, the communication log entry corresponding to the communication and the received patient alert;
providing for display, via the GUI, a set of patient contexts associated with the received patient alert in response to the generation of the communication log entry; and
responsive to receiving a selection of at least one of the displayed set of patient contexts, causing the remote server device to modify a remotely stored electronic medical record associated with the received patient alert based on the selected at least one of the displayed set of patient contexts and the generated communication log entry.

2. The one or more non-transitory computer storage media of claim 1, further comprising:
responsive to selection of the received patient alert, retrieving the set of patient contexts from the remotely stored electronic medical record.

3. The one or more non-transitory computer storage media of claim 1, wherein the initiated communication with the remote computing device comprises an audio signal.

4. The one or more non-transitory computer storage media of claim 1, wherein the initiated communication with the remote computing device comprises a text message.

5. The one or more non-transitory computer storage media of claim 1, further comprising:
initiating a different communication with another remote computing device; and
communicating the communication log entry and the selected at least one patient context to the other remote computing device.

6. The one or more non-transitory computer storage media of claim 1, wherein a search bar operable to search the plurality of patient contexts is also presented, via the GUI, based at least in part on the received first selection.

7. The one or more non-transitory computer storage media of claim 1, wherein the computing device is a mobile telecommunications device.

8. A computer-implemented method comprising:
receiving, by a first computing device, communicated by a remote server device monitoring a plurality of patients through a network, the data including a patient alert and a plurality of contacts that is populated based on the patient alert;
responsive to input received by the first computing device representative of selection of the received patient alert, providing for display a contact list including the plurality of contacts via a graphical user interface (GUI);
responsive to selection of a particular contact from the displayed contact list, initiating a communication between the first computing device and a remote computing device associated with the particular contact;
responsive to a determination that the initiated communication with the remote computing device has terminated, generating a communication log entry, the communication log entry corresponding to the communication and the received patient alert;
providing for display, by the first computing device and via the GUI, a set of patient contexts associated with the received patient alert in response to the generation of the communication log entry; and
responsive to receiving a selection of at least one of the displayed set of patient contexts, causing a remote server device to modify a remotely stored electronic medical record associated with the received patient alert based on the selected at least one of the displayed set of patient contexts and the generated communication log entry.

9. The method of claim 8, further comprising:
initiating communication with another remote computing device; and
communicating the generated communication log entry and the selected at least one patient contexts to the second remote computing device.

10. The method of claim 8, wherein the set of patient contexts are received from the remote server device via a wireless telecommunications network.

11. The method of claim 8, wherein the initiated communication includes any one of a telephone call or an electronic message.

12. The method of claim 8, wherein at least the portion of the obtained plurality of patient contexts for selection is presented based on a search parameter received via a search bar also presented in response to the determination that the communication with the remote computing device is terminated.

13. The non-transitory computer storage media of claim 1 wherein the patient alert is generated in response to medical data received from a medical device associated with the particular patient.

14. A system for tracking communications in a remote electronic medical record (EMR) system, the system comprising:
one or more processors;
one or more non-transitory computer storage media storing computer-executable instructions that, when executed by the one or more processors, cause the one or more processors to perform operations comprising;
receiving data including a patient alert and a plurality of contacts, the data communicated by a remote server device monitoring a plurality of patients through a network;
responsive to selection of the received patient alert, providing for display a contact list including the plurality of contacts via a graphical user interface (GUI;
responsive to selection of a particular contact from the displayed contact list, initiating communication with a first remote computing device associated with the particular contact list;
automatically generating a communication log entry corresponding to communication with the first remote computing device based on detecting that the initiated communication has terminated;
responsive to generation of the communication log entry, retrieving a set of patient contexts associated with the received patient alert from an EMR stored in a remote EMR system; and
responsive to selection of at least one patient context of the set of patient contexts, automatically modifying the EMR stored in the remote EMR system with the at least one selected patient contexts and the generated communication log entry.

15. The system of claim 14, wherein retrieving the set of patient contexts is based on a locally initiated search query of the remote EMR system.

16. The system of claim 14, further comprising:
initiating communication with a second remote computing device; and
communicating the generated communication log entry and the selected at least one patient contexts to the second remote computing device.

17. The system of claim 14, wherein the initiated communication with the first remote computing device comprises a text message.

18. The system of claim 14, wherein the initiated communication with the first remote computing device comprises an audio signal.

* * * * *

UNITED STATES PATENT AND TRADEMARK OFFICE
CERTIFICATE OF CORRECTION

PATENT NO. : 11,164,673 B2
APPLICATION NO. : 14/551555
DATED : November 2, 2021
INVENTOR(S) : Vaglio et al.

Page 1 of 1

It is certified that error appears in the above-identified patent and that said Letters Patent is hereby corrected as shown below:

On the Title Page

Page 4, item (56) Column 1, Line 21: Delete "UR:" and insert --URL:--.

In the Drawings

Sheet 4 of 21, Reference Numeral 428, FIG. 4, Line 1: Delete "PHARMARCY" and insert --PHARMACY--.

Sheet 7 of 21, FIG. 7, Line 2: Delete "SERVERITY" and insert --SEVERITY--.

Sheet 7 of 21, FIG. 7, Line 9: Delete "AMMENITIES." and insert --AMENITIES.--.

Sheet 7 of 21, FIG. 7, Line 16: Delete "AMMENITIES." and insert --AMENITIES.--.

Sheet 7 of 21, FIG. 7, Line 19: Delete "AMMENITIES." and insert --AMENITIES.--.

In the Specification

Column 7, Line 66: After "display" delete "are".

In the Claims

Column 12, Line 43: In Claim 8, after "device," insert --data--.

Column 13, Line 22: In Claim 13, Before "non-transitory computer storage media" insert --One or more--.

Column 14, Line 3: In Claim 14, delete "(GUI;" and insert --(GUI)--.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*